(12) United States Patent
Kim et al.

(10) Patent No.: US 12,016,930 B2
(45) Date of Patent: *Jun. 25, 2024

(54) SKIN-PERMEATING CARRIER CONTAINING NUCLEIC ACID COMPLEX AND USE THEREOF

(71) Applicant: Seasun Therapeutics, Inc., Daejeon (KR)

(72) Inventors: Hye Joo Kim, Daejeon (KR); Ji-Yeon Yu, Chungcheongbuk-do (KR); Dong In Lee, Daejeon (KR); Yusun Kang, Daejeon (KR); Hee Kyung Park, Daejeon (KR)

(73) Assignee: SEASUN THERAPEUTICS, INC., Daejeon (KR)

( * ) Notice: Subject to any disclaimer, the term of this patent is extended or adjusted under 35 U.S.C. 154(b) by 990 days.

This patent is subject to a terminal disclaimer.

(21) Appl. No.: 16/968,378

(22) PCT Filed: Jan. 8, 2019

(86) PCT No.: PCT/KR2019/000246
§ 371 (c)(1),
(2) Date: Aug. 7, 2020

(87) PCT Pub. No.: WO2019/156366
PCT Pub. Date: Aug. 15, 2019

(65) Prior Publication Data
US 2021/0177984 A1    Jun. 17, 2021

(30) Foreign Application Priority Data
Feb. 8, 2018   (KR) .................. 10-2018-0015751

(51) Int. Cl.
| | | |
|---|---|---|
| *A61K 38/00* | (2006.01) | |
| *A61K 9/00* | (2006.01) | |
| *A61K 47/54* | (2017.01) | |
| *A61K 47/64* | (2017.01) | |
| *A61P 17/00* | (2006.01) | |
| *A61P 17/02* | (2006.01) | |
| *A61P 17/06* | (2006.01) | |
| *A61P 35/04* | (2006.01) | |
| *C12N 15/113* | (2010.01) | |
| *A61K 48/00* | (2006.01) | |

(52) U.S. Cl.
CPC ........ *A61K 47/6455* (2017.08); *A61K 9/0014* (2013.01); *A61K 47/549* (2017.08); *A61P 17/00* (2018.01); *A61P 17/02* (2018.01); *A61P 17/06* (2018.01); *A61P 35/04* (2018.01); *C12N 15/113* (2013.01); *C12N 15/1138* (2013.01); *A61K 48/00* (2013.01); *C12N 2310/11* (2013.01); *C12N 2310/14* (2013.01); *C12N 2310/3513* (2013.01); *C12N 2310/3519* (2013.01)

(58) Field of Classification Search
CPC .. A61K 45/06; A61K 47/549; A61K 47/6455; A61K 48/00; A61K 9/0014; A61K 31/7052; A61K 31/7088; A61K 31/713; A61K 47/64; A61K 48/0041; A61P 17/00; A61P 17/02; A61P 17/06; A61P 35/04; A61P 27/02; A61P 3/00; A61P 3/10; A61P 35/00; A61P 9/00; A61P 9/10; C12N 15/111; C12N 15/113; C12N 15/1138; C12N 15/87; C12N 2310/11; C12N 2310/04; C12N 2310/3181; C12N 2310/3513; C12N 2310/3519; C12N 2320/32; C12Q 1/6883; C12Q 1/6886
See application file for complete search history.

(56) References Cited

U.S. PATENT DOCUMENTS

| | | |
|---|---|---|
| 4,235,871 A | 11/1980 | Papahadjopoulos et al. |
| 4,501,728 A | 2/1985 | Geho et al. |
| 4,837,028 A | 6/1989 | Allen |

(Continued)

FOREIGN PATENT DOCUMENTS

| | | | | |
|---|---|---|---|---|
| CN | 105463002 A | * | 4/2016 | ............. A61K 47/48 |
| CN | 105463002 A | | 4/2016 | |

(Continued)

OTHER PUBLICATIONS

Martin et al. (AAPS Journal 2007; 9 (1) Article 3). Peptide-guided Gene Delivery (Year: 2007).*

(Continued)

*Primary Examiner* — Aradhana Sasan
*Assistant Examiner* — Mercy H Sabila
(74) *Attorney, Agent, or Firm* — HULTQUIST, PLLC; Steven J. Hultquist

(57) ABSTRACT

A skin-penetrating carrier containing a nucleic acid complex having a novel structure which introduces a bioactive nucleic acid into cells. Composition for diagnosing, preventing or treating disease and to a skin-penetrating carrier containing a nucleic acid complex in which a bioactive nucleic acid and a carrier peptide nucleic acid are complementarily bound to each other, and having skin permeability and skin retention ability. Skin-penetrating carrier containing nucleic acid complex having structure of Structural Formula (1) has both a skin penetration function of effectively delivering a large-molecular-weight drug and in vivo effectiveness. Carrier enables bioactive nucleic acids or various compounds to pass through the epidermis and dermis of the skin, thus enables external treatment by application to the skin surface.

22 Claims, 22 Drawing Sheets
Specification includes a Sequence Listing.

(56) References Cited

U.S. PATENT DOCUMENTS

| | | | |
|---|---|---|---|
| 5,019,369 | A | 5/1991 | Presant et al. |
| 5,719,262 | A | 2/1998 | Buchardt et al. |
| 10,745,446 | B2 * | 8/2020 | Jeo .................. C12N 15/111 |
| 2019/0185519 | A1 * | 6/2019 | Jeo .................. C12N 15/111 |
| 2022/0125935 | A1 * | 4/2022 | Yu .................. A61K 9/0014 |

FOREIGN PATENT DOCUMENTS

| | | | |
|---|---|---|---|
| JP | 2008220336 A | | 9/2008 |
| JP | 2008220366 A | * | 9/2008 |
| JP | 2008220366 A | | 9/2008 |
| JP | 2000503671 A | | 3/2020 |
| JP | 6818889 B | | 1/2021 |
| KR | 101228106 B1 | | 7/2011 |
| KR | 1020140041438 A | | 4/2014 |
| WO | 2018030789 A1 | | 2/2018 |

OTHER PUBLICATIONS

English language translation of the JP2008220366A publication obtained by Esapcenet (Year: 2008).*

English language translation of the CN105463002A publication obtained by Google patent (Year: 2016).*

Office Action in counterpart Chinese Patent Application No. 201980028880.4, dated Oct. 8, 2022.

Li, M., et al., "Discovery and Characterization of a Peptide That Enhances Endosomal Escape of Delivered Proteins in Vitro and in Vivo", Journal of the American Chemical Society, 2015, pp. 14084-14093; DOI:10.1021/jacs.5b05694, vol. 137, Publisher: ACS Publications.

Noboru Sotoishi, "Development and Evaluation of Non-invasive Devices", Pharmacia, pp. 774-779, vol. 49, No. 8, Publisher: 2013.

Kole R. et al., "RNA therapeutics: beyond RNA interference and antisense oligonucleotides", Nature Reviews. Drug Discovery, 2012; 11; 125-140.

Wilson C. et al., "Building oligonucleotide therapeutics using non-natural chemistries", Current Opinion in Chemical Biology, 2006; 10: 607-614.

Joergensen M. et al., "Efficiency of Cellular Delivery of Antisense Peptide Nucleic Acid by Electroporation Depends on Charge and Electroporation Geometry", Oligonucleotides 2011, 21; 29-37.

Couto L. B. et al., "Viral vector-mediated RNA interference", Current Opinion in Pharmacology, 2010, 5; 534-542.

Zhi D. et al., "The Headgroup Evolution of Cationic Lipids for Gene Delivery", Bioconjugate Chemistry, 2013, 24; 487-519.

Buyens K. et al., "Liposome based systems for systemic siRNA delivery: Stability in blood sets the requirements for optimal carrier design", Journal of Controlled Release, 2012, 158; 362-70.

Rossi, J. J. et al., "SNALPing siRNAs in vivo", Gene Therapy, 2006, 13: 583-584.

Yousefi A. et al., "Trends in polymeric delivery of nucleic acids to tumors", Journal of Controlled Release, 2013, 170; 209-18.

Trabulo S. et al., "Cell-penetrating Peptides as Nucleic Acid Delivery Systems: From Biophysics to Biological Applications", Current Pharmaceutical Design, 2013, 19; 2895-923.

D. W. Pack, A. S. Hoffman, S. Pun, P. S. Stayton, "Design and development of polymers for gene delivery," Nat. Rev. Drug. Discov., 4, 581-593, 2005.

Szoka et al., "Comparative Properties and Methods of Preparation of Lipid Vesicles (Liposomes) l", Ann. Rev. Biophys. Bioeng., 9:467, 1980.

Lademann et al., "Nanoparticles—An efficient carrier for drug delivery into the hair follicles", European Journal Pharmaceutics and Biopharmaceutics, May 2007; 66(2):159-64.

Chen et al., 2006a "Ligands Regulate Cell Surface Level of the Human Opioid Receptor by Activation-Induced Down-Regulation and Pharmacological Chaperone-Mediated Enhancement: Differential Effects of Nonpeptide and Peptide Agonists", The Journal of Pharmacology Experimental Therapeutics, Nov. 2006;319(2):765-75.

Chen et al., "Transdermal protein delivery by a coadministered peptide identified via phage display", 2006b, Nature Biotechnology, Apr. 2006; 24(4):455-60.

Koppelhus, U. et al., "Cellular delivery of peptide nucleic acid (PNA)", Advanced Drug Delivery Reviews, 2003, 55: 267-280.

Mitra, R. et al., "Aminomethylene Peptide Nucleic Acid (am-PNA): Synthesis, Regio-/ Stereospecific DNA Binding, And Differential Cell Uptake of ($\alpha/\gamma$,R/ S)am-PNA Analogues", Journal of Organic Chemistry, 2012, 77: 5696-5704.

Sugiyama et al, "Chiral Peptide Nucleic Acids with a Substituent in the N-(2-Aminoethy)glycine Backbone", "XP055411282, DOI: 10.3390/molecules18010287", Dec. 27, 2012, pp. 287-310, vol. 18, No. 1, Publisher: Molecules.

* cited by examiner

SC : stratum corneum (각질층)
ED : Epidermis (표피층)
D : Dermis (진피층)

1h-antisense with full carrier : various conditions 1h-antisense with short carrier : various conditions

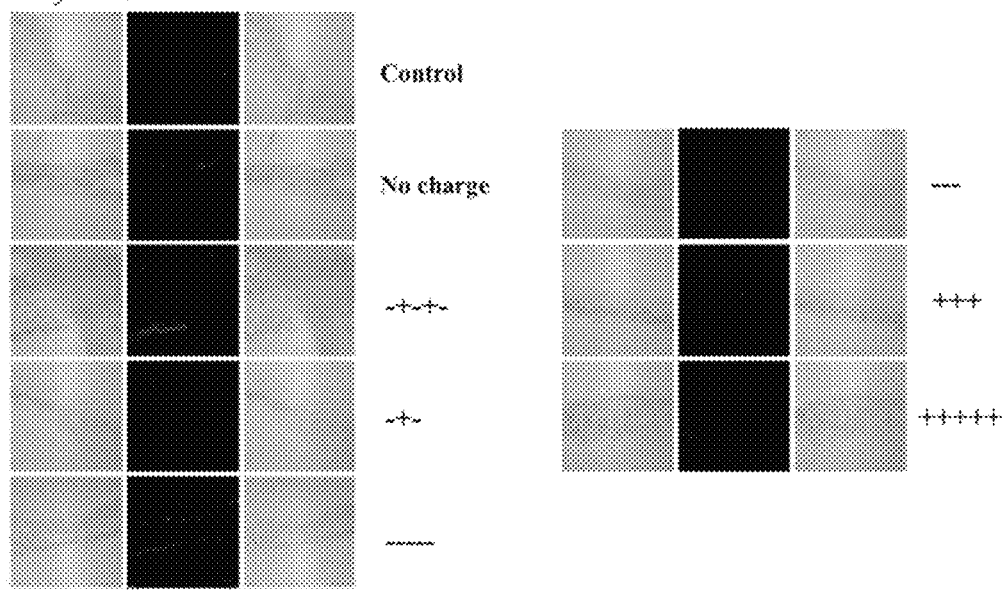
3h–antisense with full carrier: various conditions
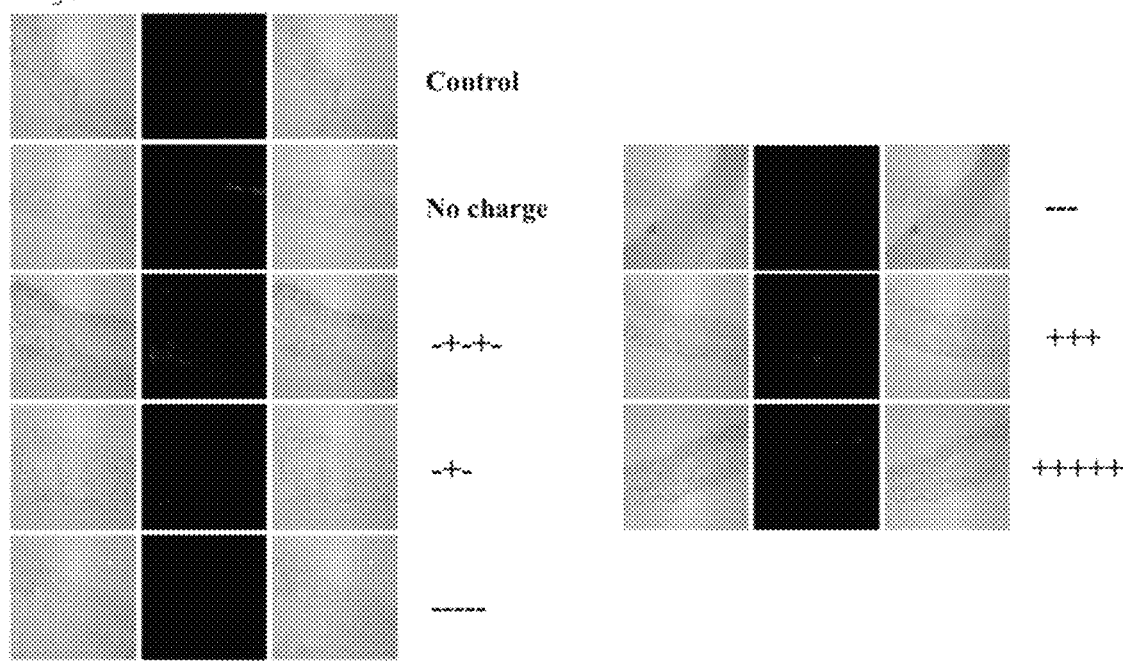
3h–antisense with short carrier: various conditions 24h -antisense with full carrier : various conditions 24h -antisense with short carrier : various conditions 1h –antisense with carrier charge (full carrier) : various conditions 3h –antisense with carrier charge (full carrier) : various conditions 24h –antisense with carrier charge (full carrier) : various conditions 1h –antisense with carrier length : various conditions Control 7 mer 9 mer 11 mer 13 mer 3h –antisense with carrier length : various conditions Control 7 mer 9 mer 11 mer 13 mer 24h –antisense with carrier length : various conditions 1 Day 2 Day Control     TGFβ-1

1 Day

2 Day

PNA #1     PNA #2     PNA #3

❖ 1-5 : modified PNA duplex
(short carrier(triazole)/short carrier/modified short carrier/Full carrier/modified full carrier)

❖ 6-10 : conventional PNA duplex
(short carrier(triazole)/short carrier/modified short carrier/Full carrier/modified full carrier)

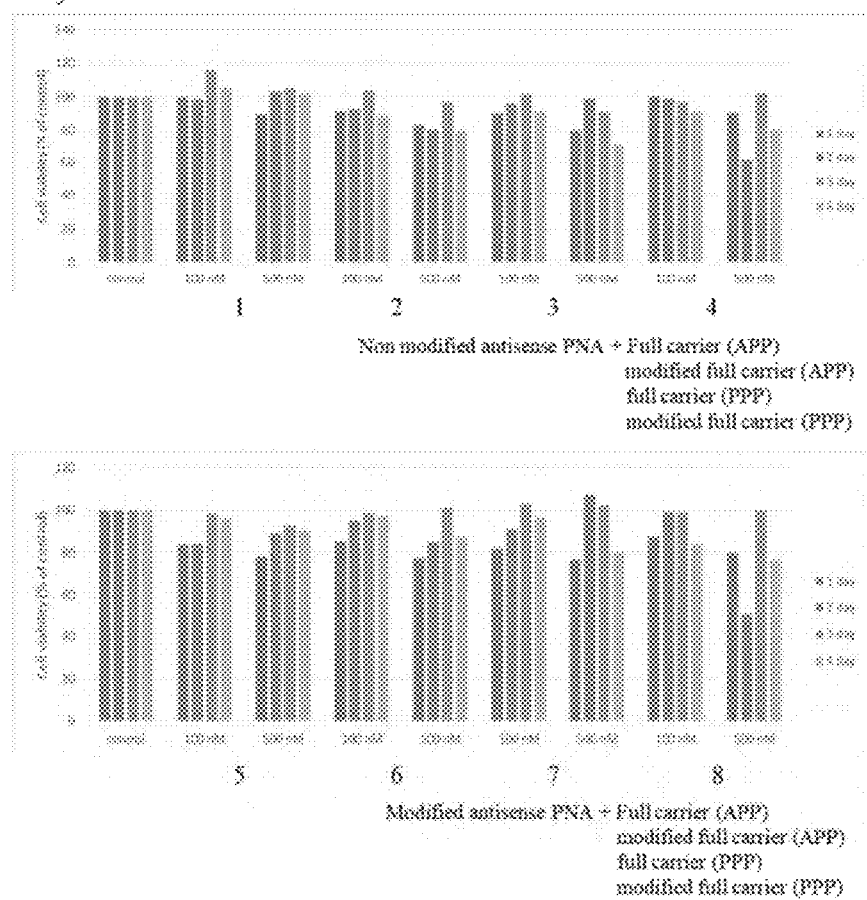

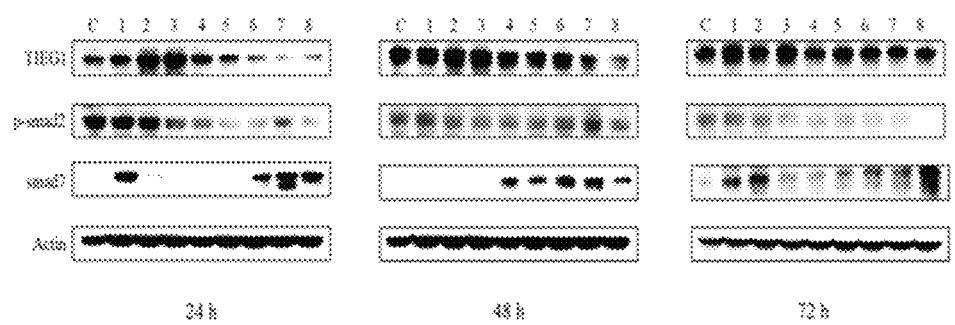

SKIN-PERMEATING CARRIER CONTAINING NUCLEIC ACID COMPLEX AND USE THEREOF

CROSS-REFERENCE TO RELATED APPLICATIONS

This United States application is the National Phase of PCT Application No. PCT/KR2019/000246 filed 8 Jan. 2019, which claims priority to South Korean Patent Application No. 10-2018-0015751 filed 8 Feb. 2018, each of which is incorporated herein by reference.

REFERENCE TO SEQUENCE LISTING

The Applicant directs entry of the revised sequence listing into the application.

The materials in the sequence listing filed with this application are incorporated herein by reference.

The name of the sequence listing file is 'SequenceLis146282.txt'. The document creation date is 9 Nov. 2020. The size of the document is 9.57 KB (9.800 bytes).

TECHNICAL FIELD

The present invention relates to a skin-penetrating carrier containing a nucleic acid complex capable of introducing a bioactive nucleic acid into cells, and a composition for diagnosing, preventing or treating disease comprising the same, and more particularly to a skin-penetrating carrier containing a nucleic acid complex in which a bioactive nucleic acid and a carrier peptide nucleic acid are complementarily bound to each other, and having skin permeability and skin retention ability, and a composition for diagnosing, preventing or treating disease comprising the same.

BACKGROUND ART

Unlike traditional drugs, nucleic acid drugs inhibit the expression of target-specific messenger RNA (mRNA), making it possible to address research areas in which diseases could not be treated by conventional drugs that target proteins (Kole R. et al., Nature Rev. Drug Discov. 2012; 11; 125-140, Wilson C. et al., Curr. Opin. Chem. Bio. 2006; 10: 607-614.).

Despite the excellent effects and various applications of gene expression regulation based on oligonucleic acid, there are many obstacles to overcome in the development of nucleic acid-based therapeutic agents. For example, oligonucleic acid can be damaged by nuclease or the like, and the passage of oligonucleic acids through the cell membrane by passive diffusion is impossible due to the electrical properties (charges) and size of these oligonucleic acids. In order to overcome these problems, efforts have been continuously made to ensure biological stability through modification of nucleic acids. For modified artificial nucleic acids, it becomes possible to increase their affinity for target nucleic acids without loss of biological activity.

Peptide nucleic acid (PNA), a type of modified artificial nucleic acid, is an artificial nucleic acid having a (2-aminoethyl)-glycine peptide backbone introduced therein, and has the property of strongly binding to RNA and DNA, each having a nucleotide sequence complementary thereto. Particularly, the peptide nucleic acid is resistant to nuclease and has high biological stability, and studies on therapeutic agents based on various oligonucleic acids have been conducted. However, the peptide nucleic acid has the disadvantage of being difficult to introduce into cells, because it is electrically neutral (Joergensen M. et al., Oligonucleotides 2011, 21; 29-37).

The cell membrane permeability of oligonucleic acids is considerably low, and in particular, DNA or RNA is negatively charged. For this reason, these oligonucleic acids cannot pass through the hydrophobic phospholipid bilayer of the cell membrane, and thus delivery thereof into cells through simple diffusion is difficult. The use of a virus carrier such as retrovirus or AAV (adeno-associated virus) makes it possible to introduce oligonucleic acids into cells, but has risks, such as unintended immune activity and the possible recombination of oncogenes (Couto L. B. et al., Curr. Opin. Pharmacol. 2010, 5; 534-542.).

For this reason, development of nucleic acid carriers based on non-viral oligonucleic acids having low cytotoxicity and low immune activity is of increasing importance. As a result, techniques of introducing nucleic acids using cationic lipids, liposomes, stable nucleic acid lipid particles (SNALPs), polymers and cell-penetrating peptides have been developed (Zhi D. et al., Bioconjug. Chem. 2013, 24; 487-519, Buyens K. et al., J. Control Release, 2012, 158; 362-70, ROSSI, J. J. et al., Gene Ther. 2006, 13: 583-584, Yousefi A. et al., J. Control Release, 2013, 170; 209-18, Trabulo S. et al., Curr. Pharm. Des. 2013, 19; 2895-923.).

These nucleic acid delivery techniques have functional moieties by direct binding, include a complex formation step, and have problems associated with the endosomal escape efficiency of liposome structures, in vivo toxicity, and the like. Consequently, it is required to improve the function of introducing oligo-nucleic acids and overcome problems associated with production procedures and side effects.

Meanwhile, the skin is the organ with the largest surface area in the human body, and is a route through which drugs may be effectively delivered using appropriate methods. Thus, administration of physiologically active agents such as a therapeutic drug through the skin, commonly referred to as transdermal delivery, has received a great deal of attention due to characteristics such as a relatively simple dosage regime.

Structurally, the skin consists of two principle parts: a relatively thin outermost layer (the epidermis or epidermal layer), and a thicker inner region (the dermis or dermal layer). In particular, the outermost layer of the epidermis (the stratum corneum) consists of flattened dead cells which are filled with keratin. The regions between the flattened dead cells of the stratum corneum are filled with lipids which form lamellar phases that are responsible for the natural barrier properties of the skin. The stratum corneum, the outermost layer of the skin, acts as a natural barrier, and the skin permeability of foreign substances such as therapeutic drugs is extremely low, which makes it difficult to deliver substances which have a high molecular weight and are hydrophilic in nature.

In order to overcome the defense mechanism of the skin barrier against foreign substances in delivery of therapeutic drugs to the skin, studies on various skin penetration methods have been attempted. However, it is considered very difficult to deliver drugs through the properties of chemicals without physically damaging or irritating the skin. Due to the various advantages that can be expected of materials that overcome this difficulty, development is continuously demanded.

According to this demand, many studies on skin-penetrating vehicles such as liposomes, nanoparticles or peptide ligands for effectively delivering high-molecular-weight drugs have been reported [Lademann et al., 2007 (Eur J Pharm Biopharm. 2007 May; 66(2):159-64.), Chen et al., 2006a (J Pharmacol Exp Ther. 2006 November; 319(2):765-75.), Chen et al., 2006b (Nat Biotechnol. 2006 April; 24(4): 455-60.)]. Despite the increased development cost of the commercialization step through these studies, the efficiency and stability of the drug to be delivered cannot be guaranteed. Thus, there is a need to develop materials having both skin penetration function and in vivo effectiveness. For the effectiveness of therapeutic materials for application to the skin surface, a great deal of effort is required due to technical difficulties in enabling these materials to pass through the epidermis and dermis.

In connection with this, the present inventors found that a nucleic acid complex comprising a bioactive nucleic acid complementarily bound to a carrier peptide nucleic acid modified to be generally positively charged has a surprisingly increased cell permeability, and expression of a target gene can be very efficiently regulated using the nucleic acid complex. Based on this finding, the present inventors filed an application for a patent for a new structure having low cytotoxicity, an ability to allow a bioactive nucleic acid to permeate into cells, and an increased ability to regulate gene expression (PCT/KR2017/008636).

The present inventors have conducted extensive studies on a carrier that enhances the skin penetration and intracellular delivery of the above-described structure and a therapeutic drug, and as a result, have found that the above-described nucleic acid complex, in which a bioactive nucleic acid and a carrier peptide nucleic acid modified to be generally positively charged are complementarily bonded to each other, has the property of very efficiently passing the skin, preferably the stratum corneum and/or the epidermis, and thus this nucleic acid complex may be used as a skin-penetrating carrier, thereby completing the present invention.

The above information disclosed in this Background section is only for enhancement of understanding of the background of the present invention. Therefore, it may not contain information that forms the conventional art that is already known in the art to which the present invention pertains.

SUMMARY OF THE INVENTION

An object of the present invention is to provide a skin-penetrating carrier containing a nucleic acid complex having a novel structure, which is capable of administering a bioactive nucleic acid and/or a therapeutic drug through the skin.

Another object of the present invention is to provide a composition for diagnosing, preventing or treating disease comprising the skin-penetrating carrier.

To achieve the above object, the present invention provides a skin-penetrating carrier containing a nucleic acid complex having a structure of the following Structural Formula (1):

   Structural Formula (1)

wherein,

A represents a bioactive nucleic acid having either a sequence capable of binding to a target gene or a target gene sequence;

C represents a carrier peptide nucleic acid capable of binding to the bioactive nucleic acid;

'≡' represents complementary binding between the bioactive nucleic acid and the carrier peptide nucleic acid;

the bioactive nucleic acid represented by A is generally negatively charged or neutral;

$C^{(+)}$ indicates that the carrier peptide nucleic acid is generally positively charged; and the carrier peptide nucleic acid comprises one or more peptide nucleic acid monomers modified such that the carrier peptide nucleic acid is generally positively charged.

The present invention also provides a composition for diagnosing disease comprising the skin-penetrating carrier, and a composition for preventing or treating disease comprising the skin-penetrating carrier.

The present invention also provides a method for preventing or treating disease comprising a step of administering the skin-penetrating carrier.

The present invention also provides the use of the skin-penetrating carrier for preventing or treating disease.

The present invention also provides the use of the skin-penetrating carrier in the manufacture of a medicament for preventing or treating disease.

(a) A structure in which the bioactive nucleic acid and the carrier peptide nucleic acid are bound antiparallel to each other;

(b) a structure in which the bioactive nucleic acid and the carrier peptide nucleic acid are bound parallel to each other;

(c) a structure in which a therapeutic drug is bound to the skin-penetrating carrier;

(d) a structure in which a material (m) for facilitating endosomal escape is bound to the skin-penetrating carrier;

(e) a structure in which both a material (m) for facilitating endosomal escape and a therapeutic drug are bound to the skin-penetrating carrier.

Figure 2:
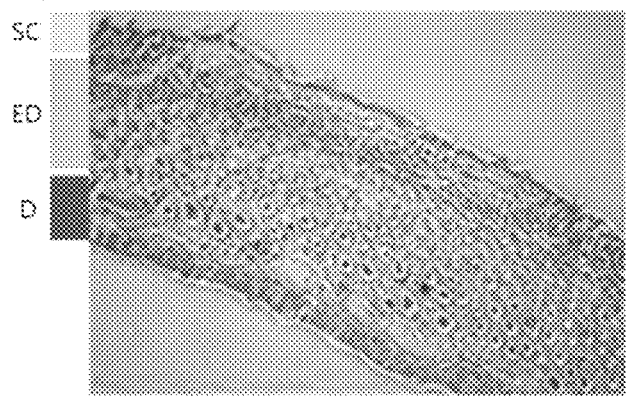

FIG. 2 illustrates the stratum corneum, epidermis and dermis of the skin.

Figure 3:
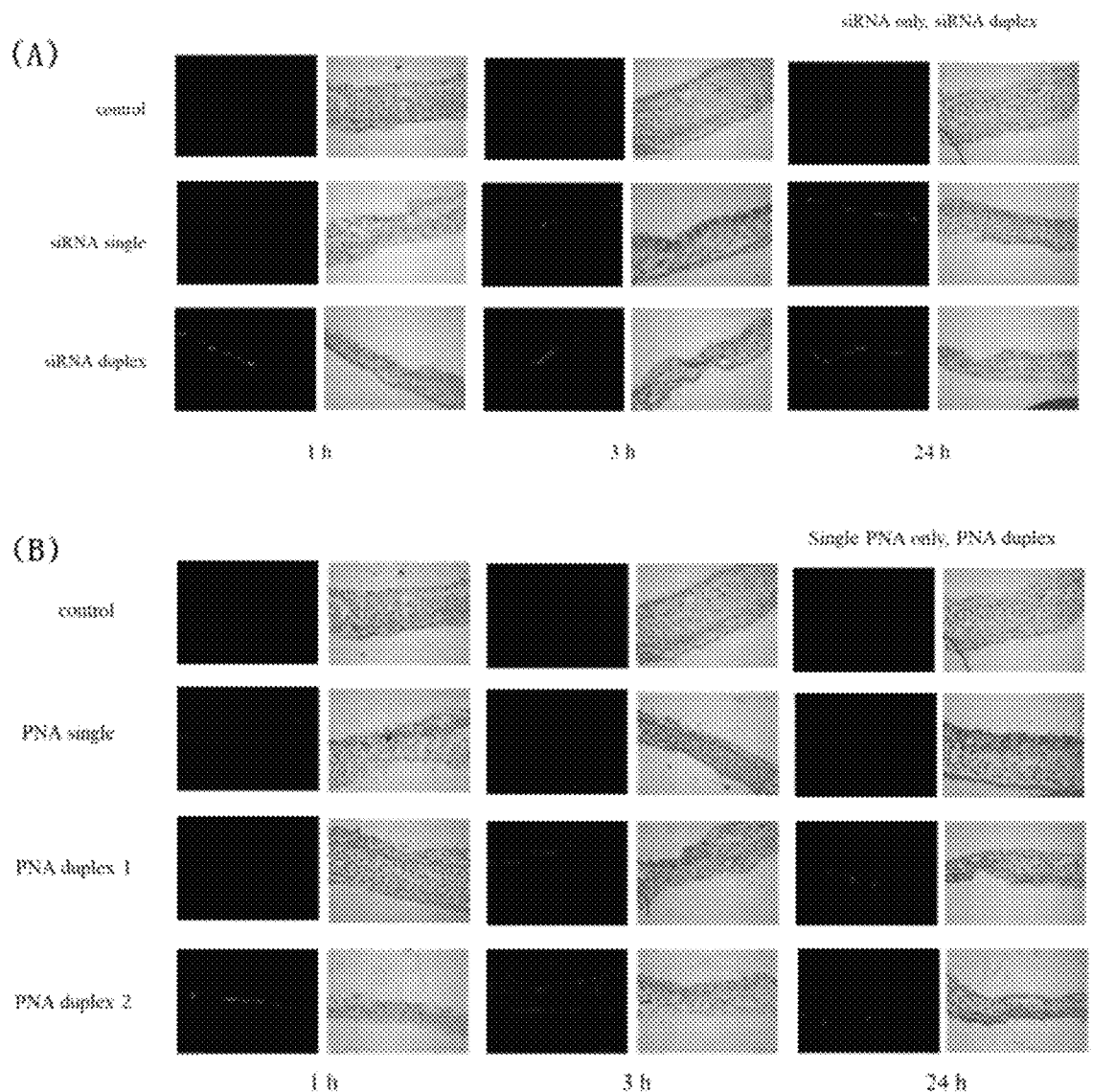
Figure 4A:
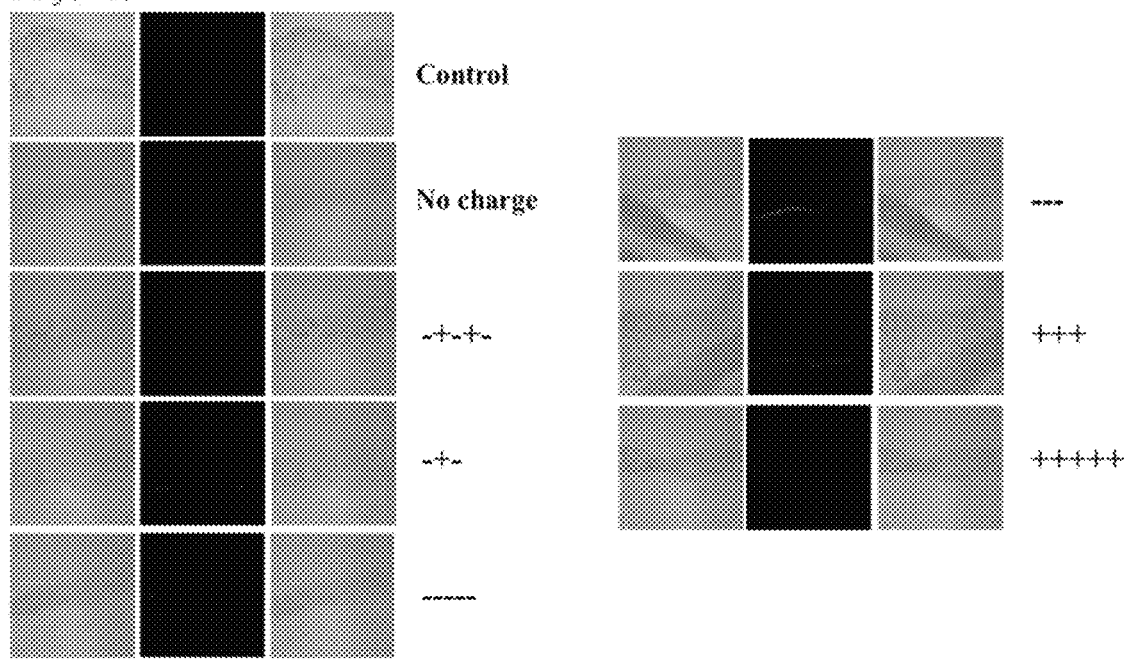
Figure 4B:
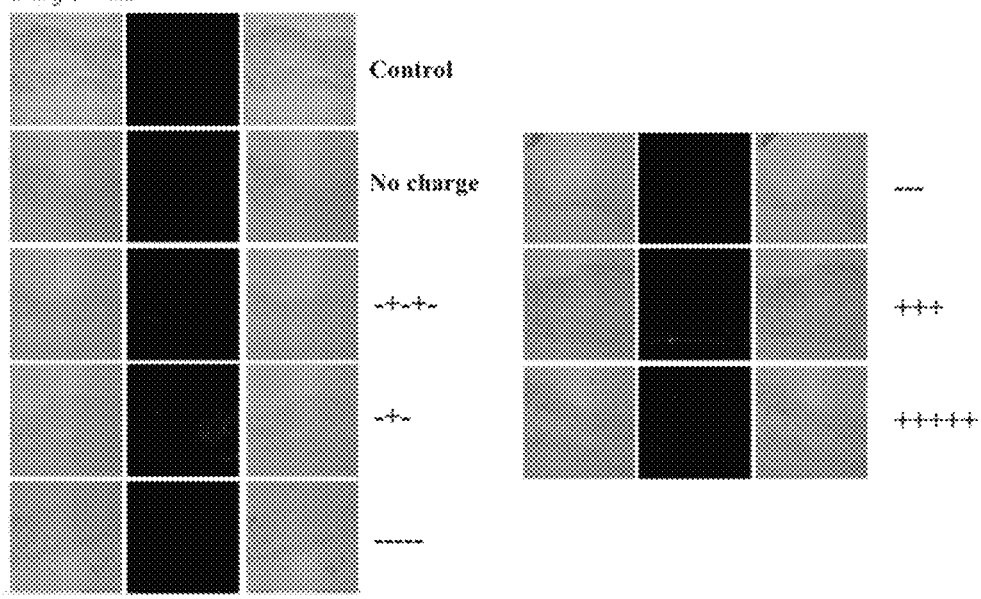
Figure 4E:
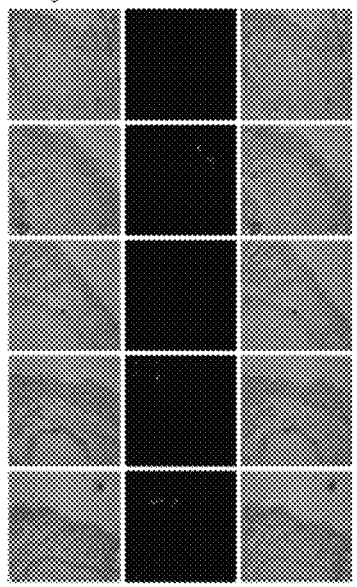
Figure 4E:
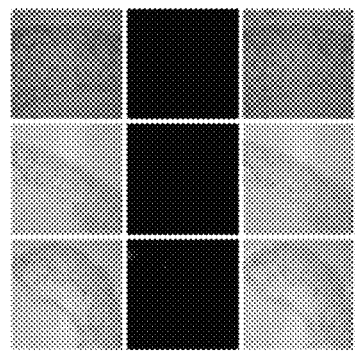
Figure 4F:
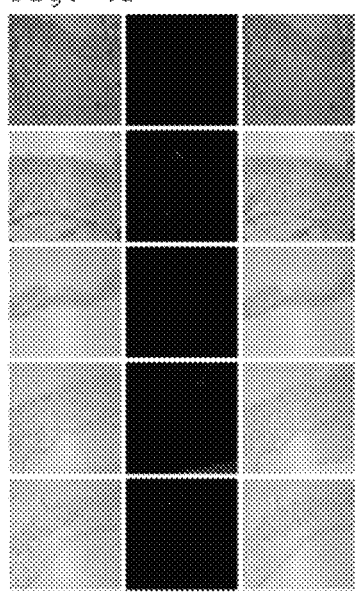
Figure 4F:
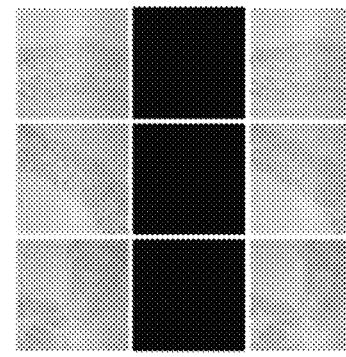
Figure 4G:
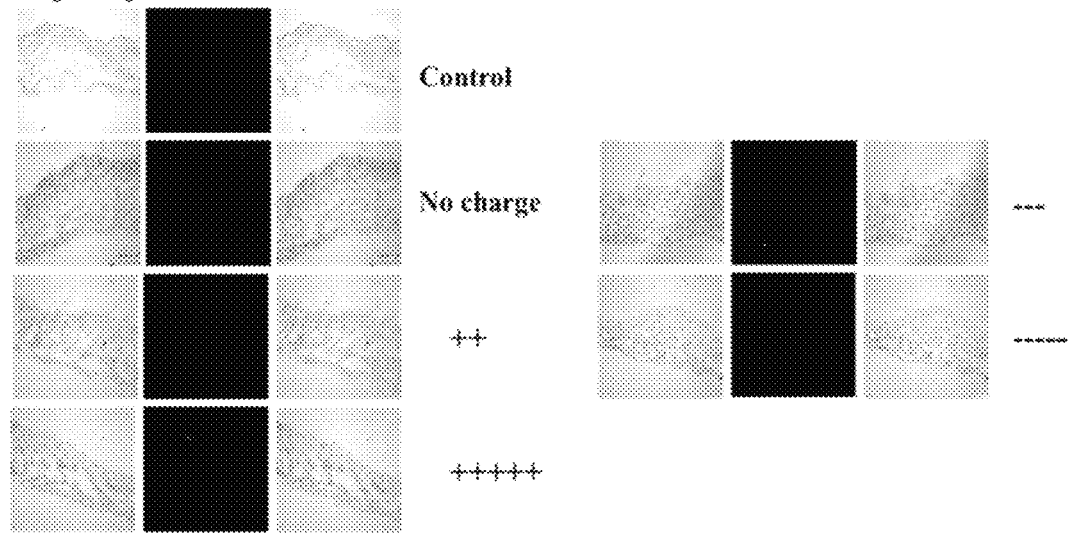
Figure 4H:
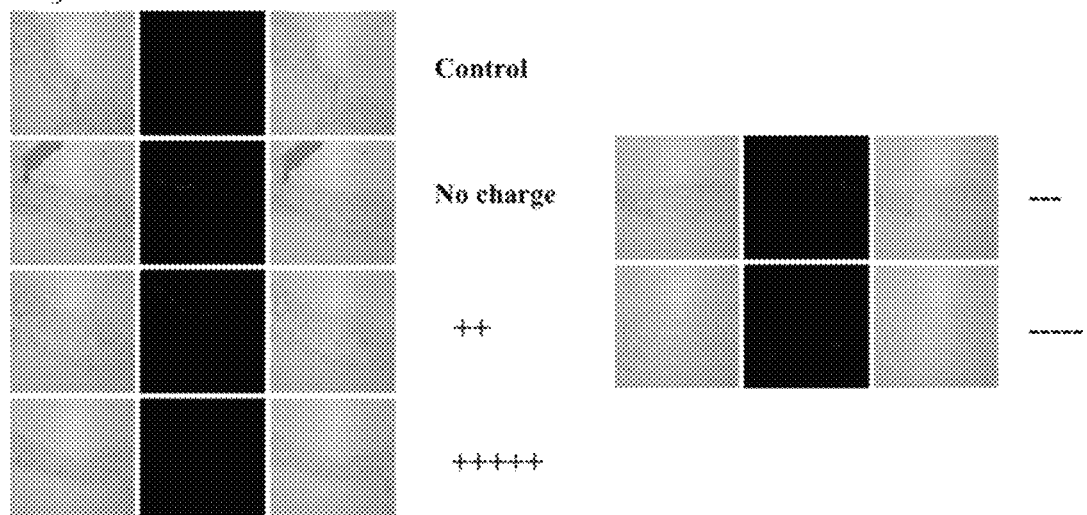
Figure 4I:
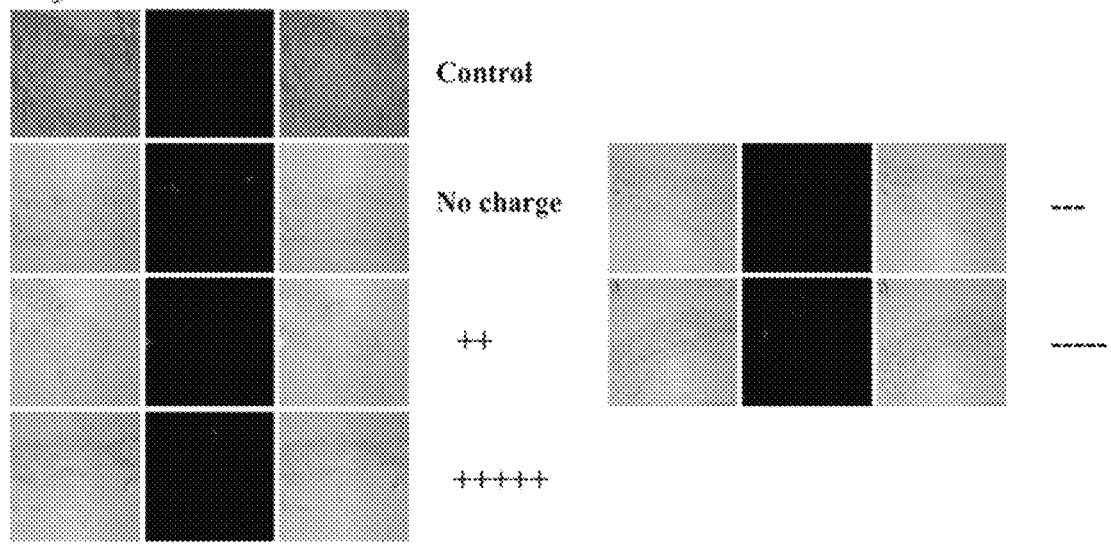
Figure 4J:
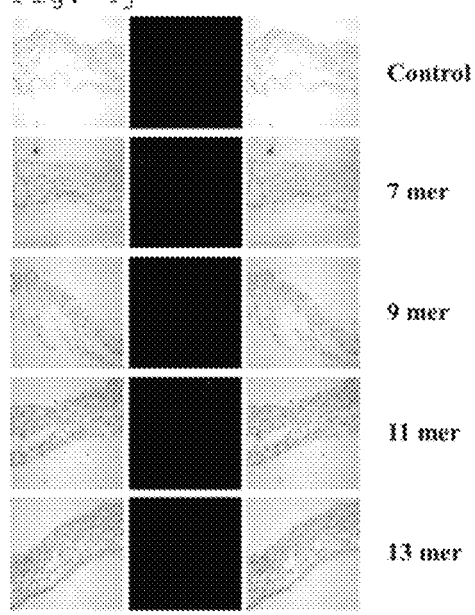
Figure 4K:
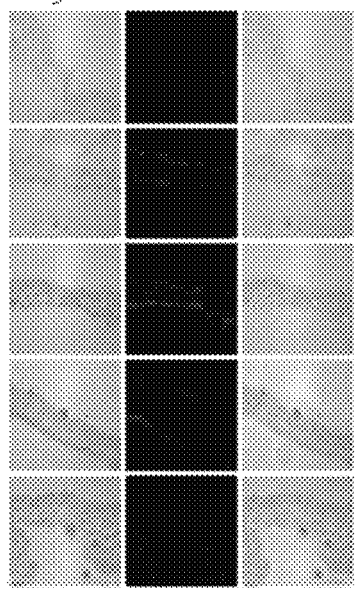
Figure 4L:
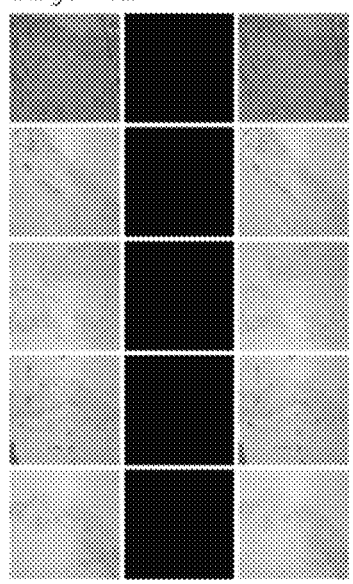

FIG. 3(A) shows the transdermal delivery ability of single siRNA and duplex siRNA, and indicates that siRNA alone was not delivered from the epidermis to the dermis, and FIG. 3(B) shows the transdermal delivery ability of a nucleic acid complex, and indicates that the nucleic acid complex was delivered from the epidermis to the dermis, and was delivered to the dermis after 24 hours.

FIGS. 4a to 4l show the results of testing the transdermal ability of cy3-labeled siRNA.

(a) Transdermal delivery ability of a nucleic acid complex one hour after treatment of the nude mouse back with the complex, in which the complex comprises a bioactive nucleic acid having a changed charge and the same length as that of a carrier peptide nucleic acid complementary thereto;

(b) transdermal delivery ability of a nucleic acid complex one hour after treatment of the nude mouse back with the complex, in which the complex comprises a bioactive nucleic acid having a changed charge and a longer length than that of a carrier peptide nucleic acid complementary thereto;

(c) transdermal delivery ability of a nucleic acid complex three hours after treatment of the nude mouse back with the complex, in which the complex comprises a bioactive nucleic acid having a changed charge and the same length as that of a carrier peptide nucleic acid complementary thereto;

(d) transdermal delivery ability of a nucleic acid complex three hours after treatment of the nude mouse back with the complex, in which the complex comprises a bioactive nucleic acid having a changed charge and a longer length than that of a carrier peptide nucleic acid complementary thereto;

(e) transdermal delivery ability of a nucleic acid complex 24 hours after treatment of the nude mouse back with the complex, in which the complex comprises a bioactive nucleic acid having a changed charge and the same length as that of a carrier peptide nucleic acid complementary thereto;

(f) transdermal delivery ability of a nucleic acid complex 24 hours after treatment of the nude mouse back with the complex, in which the complex comprises a bioactive nucleic acid having a changed charge and a longer length than that of a carrier peptide nucleic acid complementary thereto;

(g) transdermal delivery ability one hour after treatment of the nude mice back with various complexes in which carrier peptide nucleic acids having various charges are bound to generally negatively charged bioactive nucleic acids;

(h) transdermal delivery ability three hours after treatment of the nude mice back with various complexes in which carrier peptide nucleic acids having various charges are bound to generally negatively charged bioactive nucleic acids;

(i) transdermal delivery ability 24 hours after treatment of the nude mice back with various complexes in which carrier peptide nucleic acids having various charges are bound to generally negatively charged bioactive nucleic acids;

(j) transdermal delivery ability one hour after treatment of the nude mice back with various complexes in which carrier peptide nucleic acids having various lengths are bound to generally negatively charged bioactive nucleic acids;

(k) transdermal delivery ability 3 hours after treatment of the nude mice back with various complexes in which carrier peptide nucleic acids having various lengths are bound to generally negatively charged bioactive nucleic acids;

(l) transdermal delivery ability 24 hours after treatment of the nude mice back with various complexes in which carrier peptide nucleic acids having various lengths are bound to generally negatively charged bioactive nucleic acids.

Figure 5A:
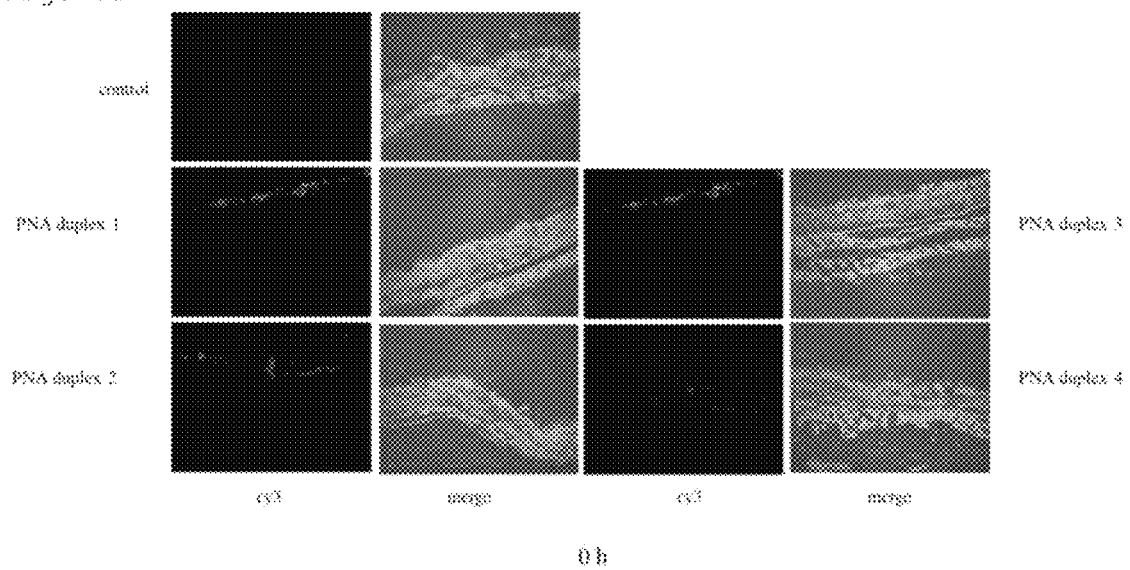
Figure 5B:
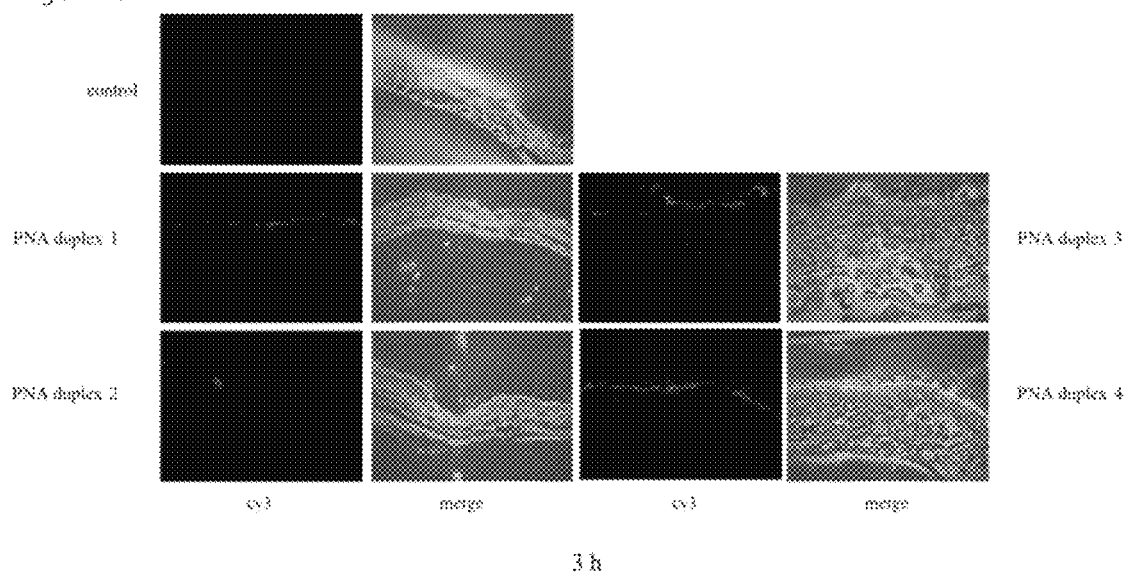
Figure 5C:
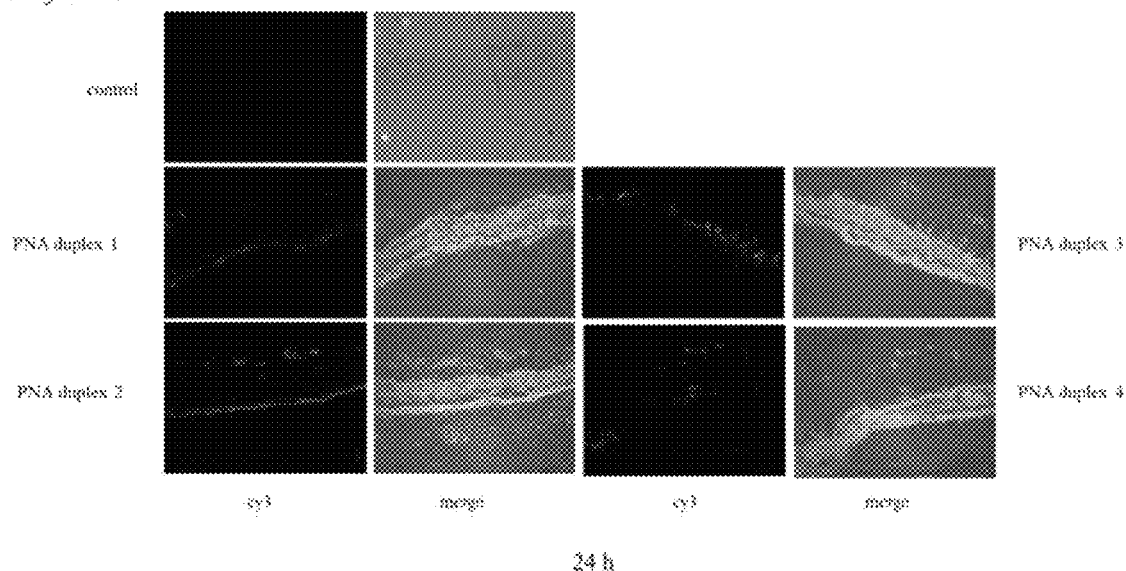

FIGS. 5a to 5c show the transdermal delivery ability of a nucleic acid complex comprising a low-molecular-weight substance.

(a) Transdermal delivery ability 0 hours after treatment with the nucleic acid complex comprising a low-molecular-weight substance;

(b) transdermal delivery ability 3 hours after treatment with the nucleic acid complex comprising a low-molecular-weight substance;

(c) transdermal delivery ability 24 hours after treatment with the nucleic acid complex comprising a low-molecular-weight substance.

FIGS. 6a to 6f show the therapeutic effect of an IFI16 gene-targeting nucleic acid complex against the skin disease, psoriasis in an in vitro experiment and an animal experiment.

(a) Cell viability in human keratinocytes induced by IL-17A, (b) expression of a target gene and downstream genes thereof in human keratinocytes induced by IL-17A, (c) images showing that the psoriasis phenotype of the mouse ear in an imiquimod-induced psoriasis animal model decreases;

(d) views showing that the mouse ear thickness in the imiquimod-induced psoriasis animal model decreases and expression of a target gene in the animal model decreases;

(e) H & E staining images showing that, in the imiquimod-induced psoriasis animal model, the epidermis thickness of mouse ear tissue, which was increased by imiquimod, is decreased by the nucleic acid complex;

(f) immunostaining images showing that, in the imiquimod-induced psoriasis animal model, expression of psoriasis markers (CD3 and CD11c) in mouse ear tissue, which was increased by imiquimod, is decreased by the nucleic acid complex.

Figure 7A:
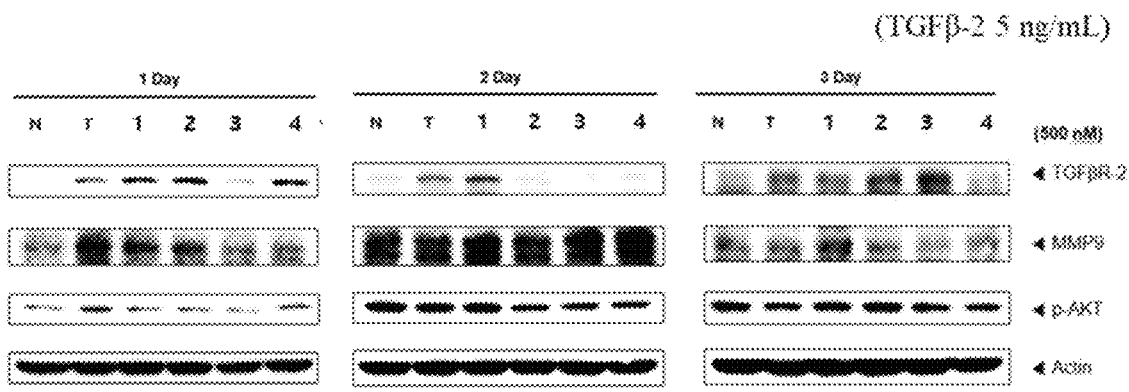
Figure 7B:
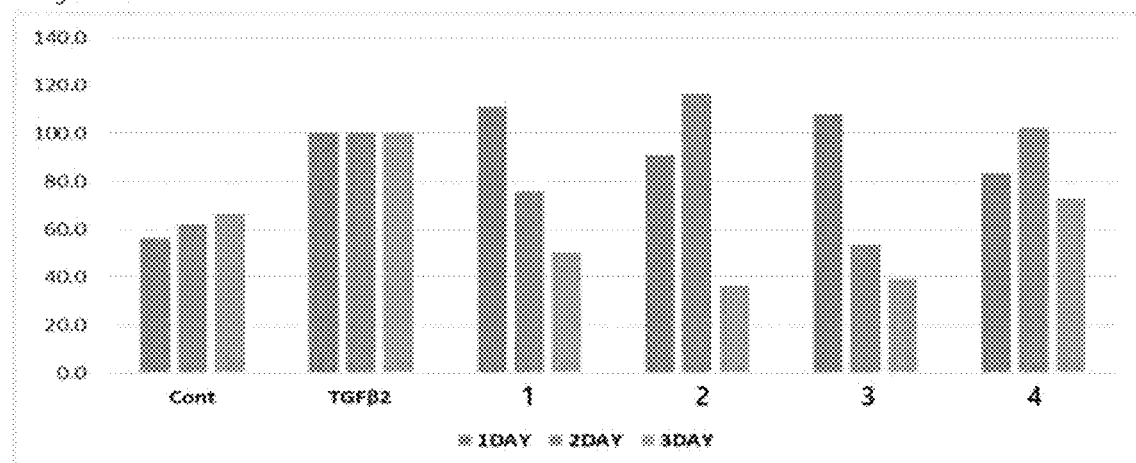

FIGS. 7a and 7b show the cell metastasis inhibitory effect of a TGFβR2 gene-targeting nucleic acid complex in metastatic skin melanoma cells (Mechanism study of anti-metastatic effect with TGFβR2 targeted PNA in vitro).

(a) Expression of a target gene and downstream genes thereof in TGFβ-2-induced metastatic skin melanoma cells;

(b) cell migration ability in TGFβ-2-induced metastatic skin melanoma cells.

FIGS. 8a to 8j show the therapeutic effects of a TLR2 gene-targeting nucleic acid complex in an atopic dermatitis mimicking cell model and an atopic dermatitis-induced animal model.

(a) Change in cell viability in human keratinocytes induced by DNCB;

(b) expression of a target gene and downstream genes thereof in human keratinocytes induced by DNCB;

(c) images showing that the atopic dermatitis phenotype of NC/Nga mice is decreased by the nucleic acid complex;

(d) views showing that, in NC/Nga mice with atopic dermatitis induced by house dust mite extract, the concentrations of IgE and TARC in serum are decreased by the nucleic acid complex;

(e) views showing that the atopic dermatitis phenotype of Balb/C mice with atopic dermatitis induced by DNCB is decreased by the nucleic acid complex;

(f) views showing that, in Balb/C mice with atopic dermatitis induced by DNCB, the concentrations of IgE and TARC in serum are decreased by the nucleic acid complex;

(g) views showing that, in NC/Nga mice with atopic dermatitis induced by house dust mite extract, the epidermis thickness is decreased by the nucleic acid complex;

(h) views showing that, in Balb/C mice with atopic dermatitis induced by DNCB, the epidermis thickness is decreased by the nucleic acid complex;

(i) views showing that the inflammatory marker CD3 in NV/Nga mice with atopic dermatitis induced by house dust mite extract is decreased by the nucleic acid complex;

(j) views showing that the inflammatory marker CD3 in NV/Nga mice with atopic dermatitis induced by DNCB is decreased by the nucleic acid complex.

Figure 9A:
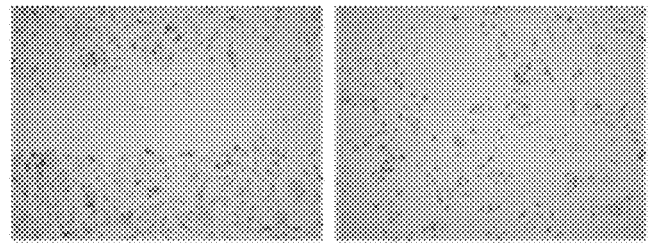
Figure 9A:
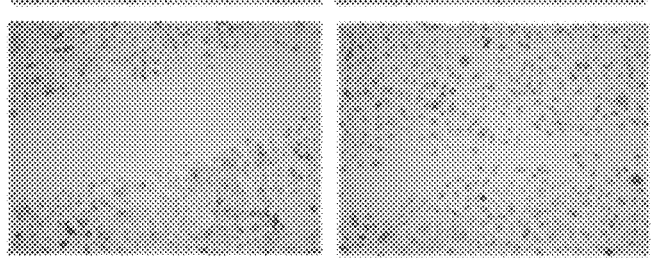
Figure 9A:
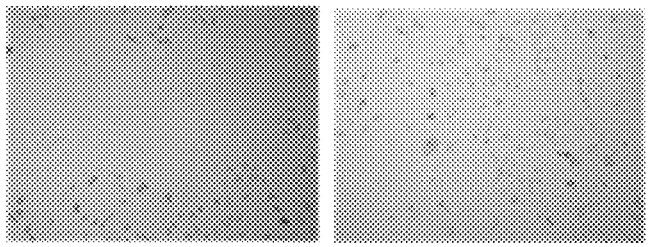
Figure 9A:
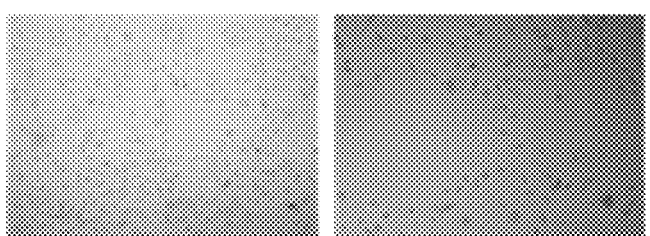
Figure 9B:
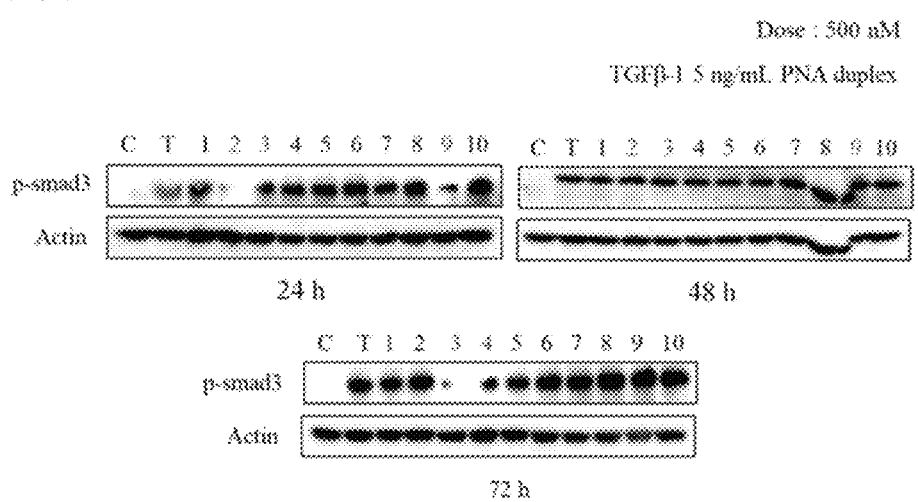

FIGS. 9a and 9b show the cell wound healing effect of a smad3 gene-targeting nucleic complex in human keratinocytes.

(a) Wound healing in human keratinocytes induced by TGFβ-1;

(b) expression of a target gene in human keratinocytes induced by TGFβ-1;

FIGS. 10a and 10b show the cell growth inhibitory effect of a TIEG1 gene-targeting nucleic acid complex in keloid fibroblasts.

(a) Cell viability in cells isolated from keloid tissue;

(b) expression of a target gene and downstream genes thereof in cells isolated from keloid tissue.

DETAILED DESCRIPTION AND PREFERRED EMBODIMENTS OF THE INVENTION

Unless otherwise defined, all technical and scientific terms used in the present specification have the same meanings as commonly understood by those skilled in the art to which the present disclosure pertains. In general, the nomenclature used in the present specification is well known and commonly used in the art.

In one example of the present invention, it has been found that a nucleic acid complex, in which a bioactive nucleic acid and a carrier peptide nucleic acid are complementarily bound to each other, has skin penetration ability and skin retention ability, and thus may be used for treatment of disease through application to the skin surface.

Therefore, in one aspect, the present invention is directed to a skin-penetrating carrier containing a nucleic acid complex having a structure of the following Structural Formula (1):

$$[A \equiv C^{(+)}] \qquad \text{Structural Formula (1)}$$

wherein,

A represents a bioactive nucleic acid having either a sequence capable of binding to a target gene or a target gene sequence;

C represents a carrier peptide nucleic acid capable of binding to the bioactive nucleic acid;

'≡' represents complementary binding between the bioactive nucleic acid and the carrier peptide nucleic acid;

the bioactive nucleic acid represented by A is generally negatively charged or neutral;

$C^{(+)}$ indicates that the carrier peptide nucleic acid is generally positively charged; and the carrier peptide nucleic acid comprises one or more peptide nucleic acid monomers modified such that the carrier peptide nucleic acid is generally positively charged.

Figure 1A:
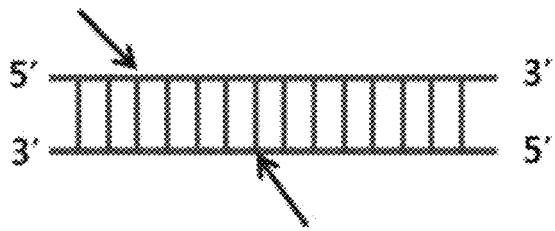
FIGS. 1a to 1e schematically show a bioactive nucleic acid and a carrier peptide nucleic acid in a skin-penetrating carrier are bound to each other.
Figure 1B:
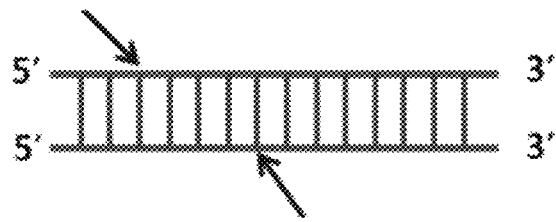

In the present invention, the bioactive nucleic acid and the carrier peptide nucleic acid in the nucleic acid complex having the structure of Structural Formula (1) may be bound to each other by anti-parallel binding or parallel binding (see FIGS. 1a and 1b).

In the present invention, "skin-penetrating carrier" is a means for delivering a bioactive substance into cells, and refers to a carrier enabling a bioactive substance to penetrate the body, ultimately cells, through contact with the skin. Specifically, the skin-penetrating carrier refers to a substance having the ability to pass through the stratum corneum (the outermost layer of the skin's epidermis) and/or the epidermis and deliver a desired drug to the epidermis or dermis, or the ability to pass even through the dermis and deliver the desired drug.

The skin-penetrating carrier according to the present invention may remain in the stratum corneum, epidermis or dermis or pass even through the dermis and deliver a desired drug into the body, depending on the net charge in the nucleic acid complex having the structure of Structural Formula (1) and/or the number of bioactive nucleic acids and/or carrier nucleic acids in the nucleic acid complex.

Therefore, in the present invention, the skin-penetrating carrier comprising the nucleic acid complex may have skin retention ability. In one example of the present invention, it was confirmed that the bioactive nucleic acid was present in the stratum corneum, epidermis and dermis of the skin.

Figure 1C:
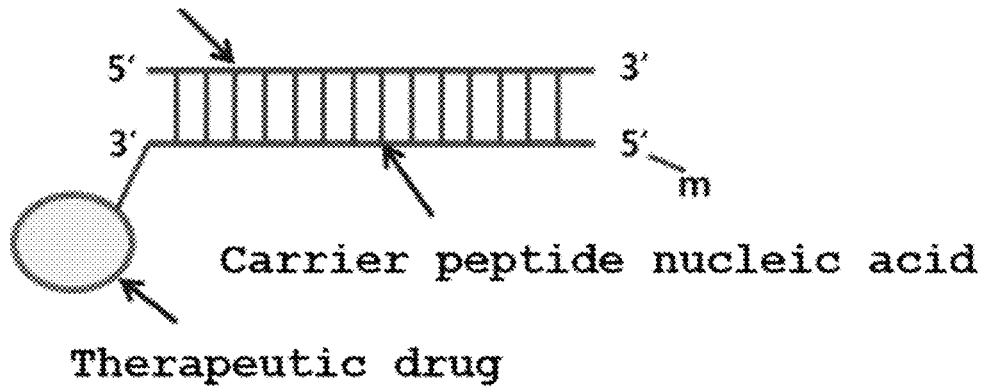

In the present invention, the bioactive nucleic acid itself in the "skin-penetrating carrier" may function as a therapeutic drug (see FIGS. 1a and 1b). Alternatively, a therapeutic drug for treatment of disease may additionally be bound to the "skin-penetrating carrier" (see FIG. 1c).

That is, the nucleic acid complex represented by Structural Formula (1) may function as both a skin-penetrating carrier and a therapeutic agent, or a therapeutic drug may also be bound to the nucleic acid complex.

In particular, the "skin-penetrating carrier" has the ability to be delivered into target cells after transdermal delivery into the body, and may be used in any form containing the nucleic acid complex.

In the present invention, "bioactive nucleic acid" refers to a nucleic acid having a complementary sequence capable of binding to a target gene whose expression is to be reduced, particularly a complementary sequence capable of binding to the mRNA of the target gene, or comprising a sequence that promotes expression of a target gene to be expressed. Specifically, it refers to a nucleic acid which is involved in gene expression regulation, such as inhibiting or promoting expression of the gene of interest. The bioactive nucleic acid may be a nucleic acid having a sequence complementary to a target gene whose expression is to be decreased or increased, or may be a nucleic acid having a sequence complementary to the sequence of a single-stranded RNA, such as pre-mRNA, miRNA, mRNA, or the like.

In particular, "bioactive nucleic acid" in the present invention may bind to a target gene or a nucleotide sequence comprising the same in vitro or in vivo, thereby activating or inhibiting the characteristic function of the target gene (e.g., transcript expression or protein expression) or regulating splicing of pre-mRNA (e.g., exon skipping). Here, the nucleotide sequence may be a gene regulatory sequence, or a gene coding sequence, or a splicing regulatory sequence. The gene regulatory sequence may be selected from among a promoter, a transcriptional enhancer, a 5' untranslated region, a 3' untranslated region, a viral packaging sequence, and a selection marker. The gene coding sequence may be an exon or an intron, and the gene coding sequence may be located within 10, 5, 3 or 1 kb or 500, 300 or 200 bp from the transcription initiation site of the gene. For example, the gene coding sequence may be located upstream or downstream of the initiation site. Furthermore, the splicing regulatory sequence may comprise a sequence associated with exon skipping, cryptic splicing, pseudo-splice site activation, intron retention, or alternative splicing deregulation.

In the present invention, "carrier peptide nucleic acid" refers to a nucleic acid whose bases partially or completely bind complementarily to the bioactive nucleic acid, thereby imparting functionality. Carrier peptide nucleic acids that may be used in the present invention include not only peptide nucleic acid (PNA), but also modified nucleic acids similar thereto. The peptide nucleic acid is preferable, but is not limited thereto.

In the present invention, the nucleic acid complex contained in the skin-penetrating carrier may further comprise a material for facilitating endosomal escape, and may have a structure of Structural Formula (2) below.

Figure 1D:
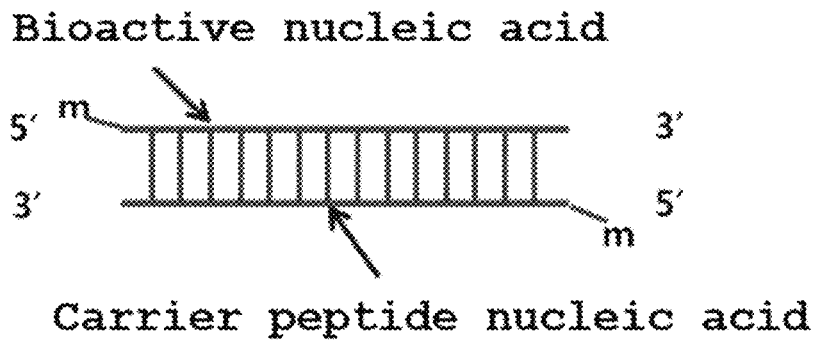
Figure 1E:
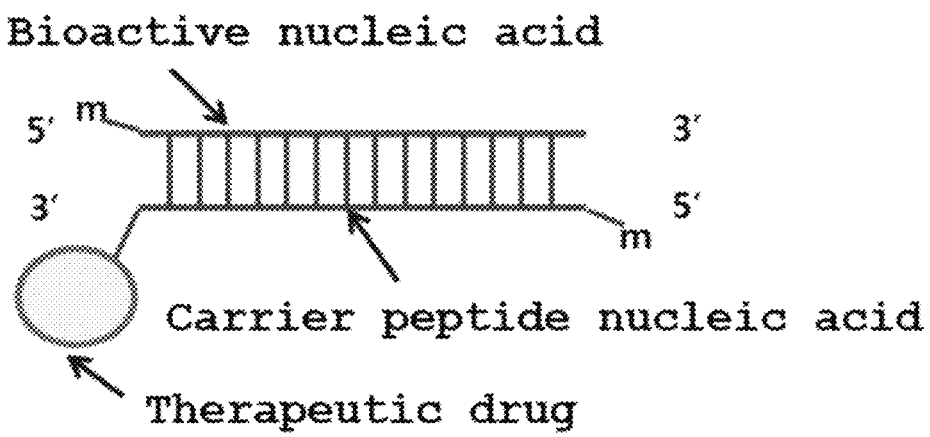

That is, the "skin-penetrating carrier" according to the present invention may have a structure to which a material for facilitating endosomal escape is bound (see Structural Formula (2) and FIGS. 1d and 1e).

$$[mA \equiv mC^{(+)}] \qquad \text{Structural Formula (2)}$$

wherein,

'm' represents a material for facilitating endosomal escape of the bioactive nucleic acid and the carrier peptide nucleic acid.

In the present invention, each of the bioactive nucleic acid and the carrier peptide nucleic acid may comprise, at the 5'-end and 3'-end thereof, the material for facilitating endosomal escape.

In the present invention, the "material for facilitating endosomal escape" may facilitate endosomal escape of the bioactive nucleic acid by increasing the osmotic pressure in endosomes or destabilizing the endosomal membrane. This means that the material helps the bioactive nucleic acid move more efficiently and quickly to the nucleus or cytoplasm so as to meet and act on a target gene (D. W. Pack, A. S. Hoffman, S. Pun, P. S. Stayton, "Design and development of polymers for gene delivery," Nat. Rev. Drug. Discov., 4, 581-593 (2005)).

As the material for facilitating endosomal escape, a peptide having the sequence of GLFDIIKKIAESF (SEQ ID NO: 49) may be bound to the bioactive nucleic acid via a linker, and histidine (10) may be bound to the carrier peptide nucleic acid via a linker, but the present invention is not limited thereto.

In the present invention, the material for facilitating endosomal escape may be any one or more selected from the group consisting of peptides, lipid nanoparticles, polyplex nanoparticles, polymer nanospheres, inorganic nanoparticles, cationic lipid-based nanoparticles, cationic polymers, and pH sensitive polymers.

In the present invention, the peptides may be selected from the group consisting of GIGAVLKVLTTGLPAL-ISWIKRKRQQ (SEQ ID NO: 48), GLFDIIKKIAESF (SEQ ID NO: 49), and histidine (10).

In the present invention, the lipid nanoparticles may be selected from the group consisting of lipids, phospholipids, cetyl palmitate, poloxamer 18, Tween 85, tristearin glyceride, and Tween 80.

In the present invention, the polyplex nanoparticles may be poly(amidoamine) or polyethylenimine (PEI).

In the present invention, the polymer nanospheres may be selected from the group consisting of polycaprolactone, poly(lactide-co-glycolide), polylactide, polyglycolide, poly(d,l-lactide), chitosan, and PLGA-polyethylene glycol.

In the present invention, the inorganic nanoparticles may be selected from the group consisting of $Fe_2O_3$ $Fe_3O_4$, $WO_3$ and $WO_{2.9}$.

In the present invention, the cationic lipid-based nanoparticles may be selected from the group consisting of 1-(aminoethyl)iminobis[N-(oleicylcysteinyl-1-amino-ethyl)propionamide], an N-alkylated derivative of PTA, and 3,5-didodecyloxybenzamidine.

In the present invention, the cationic polymer may be selected from the group consisting of vinylpyrrolidone-N,N-dimethylaminoethyl methacrylate acid copolymer diethyl sulphate, polyisobutylene, and poly(N-vinylcarbazole).

In the present invention, the pH-sensitive polymers may be selected from the group consisting of polyacids, poly(acrylic acid), poly(methacrylic acid), and hydrolyzed polyacrylamide.

In the present invention, the nucleic acid complex contained in the skin-penetrating carrier may further comprise a therapeutic drug as described above. The therapeutic drug may be, for example, one or more selected from the group consisting of therapeutic proteins, therapeutic compounds, cancer chemotherapeutic agents, toxins, cytotoxic substances, anti-inflammatory agents, arthritis treatment agents, growth factors, cytokines, chemokines, antibodies, RNAi such as siRNA or miRNA, antisense, nucleic acids, nucleic acid analogs, cells, viruses, phages, virus particles, phage particles, virus capsids, phage capsids, virus-like particles, liposomes, micelles, beads, nanoparticles, microparticles, chemotherapeutic agents, contrast agents, imaging agents, labels, labeling agents, or combinations thereof.

The therapeutic drug may be bound by a covalent bond or a linker to the nucleic acid complex contained in the skin-penetrating carrier according to the present invention.

In the present invention, each of the bioactive nucleic acid and the carrier peptide nucleic acid may comprise 2 to 50, preferably 5 to 30, more preferably 10 to 25, most preferably 15 to 17 nucleic acid monomers.

Moreover, the bioactive nucleic acid may be composed of natural nucleic acid bases and/or modified nucleic acid monomers.

In the present invention, the bioactive nucleic acid may be selected from the group consisting of DNA, RNA, and modified nucleic acids, i.e., PNA (peptide nucleic acid), PMO (phosphorodiamidate morpholino oligonucleotide), LNA (locked nucleic acid), GNA (glycol nucleic acid), TNA (threose nucleic acid), antisense oligonucleotide, aptamer, siRNA (small interfering RNA), shRNA (short hairpin RNA), ribozyme, and DNAzyme. Preferably, the bioactive nucleic acid may be selected from the group consisting of DNA, RNA, and modified nucleic acids, i.e., PNA, PMO, LNA, GNA, and TNA, but is not limited thereto.

In the present invention, when a monomer used in the bioactive nucleic acid is PNA, the bioactive nucleic acid is referred to as bioactive peptide nucleic acid, and when another monomer is used, the bioactive nucleic acid is also referred to in the same manner.

In the present invention, the bioactive nucleic acid and the carrier peptide nucleic acid may further comprise one or more functional groups selected from the group consisting of phosphodiester, 2'O-methyl, 2' methoxy-ethyl, phosphoramidate, methylphosphonate, and phosphorothioate.

In the present invention, the carrier peptide nucleic acid may have a nucleotide sequence which is partially or completely complementary to the bioactive nucleic acid. In particular, the carrier peptide nucleic acid may comprise one or more universal bases, and the carrier peptide nucleic acid may also be completely composed of universal bases.

In the present invention, each of the bioactive nucleic acid and the carrier peptide nucleic acid of the nucleic acid complex may be generally positively charged (cationic), negatively charged (anionic) or neutral.

The term "generally" as used when expressing electrical charge does not mean the electrical property of individual bases, but means the overall electrical properties of the bioactive nucleic acid or the carrier peptide nucleic acid when viewed externally. For example, if the number of negatively charged monomers in the bioactive nucleic acid is larger even though some monomers in the bioactive nucleic acid are positively charged, the bioactive nucleic acid is negatively charged when "generally" viewing the electrical property. If the number of positively charged bases and/or backbones in the carrier peptide nucleic acid is larger even though some bases and/or backbones in the carrier peptide nucleic acid are negatively charged, the carrier peptide nucleic acid is positively charged when "generally" viewing the electrical property.

In this regard, the nucleic acid complex having a structure of Structural Formula (1) according to the present invention may be generally positively charged. In the nucleic acid complex of Structural Formula (1), it is preferred that the bioactive nucleic acid be negatively charged or neutral when generally viewing the electrical property, and the carrier peptide nucleic acid be positively charged when generally viewing the electrical property. However, the present invention is not limited thereto.

The electrical property of each of the bioactive nucleic acid and the carrier peptide nucleic acid may be imparted using a modified peptide nucleic acid monomer. The modified peptide nucleic acid monomer may comprise, as positively charged carrier peptide nucleic acids, any one or more positively charged amino acids selected from the group consisting of lysine (Lys, K), arginine (Arg, R), histidine (His, H), diamino butyric acid (DAB), ornithine (Orn), and an amino acid analogue. In addition, the modified peptide nucleic acid monomer may comprise, as a negatively charged carrier peptide nucleic acid, glutamic acid (Glu, E), which is a negatively charged amino acid, or a negatively charged amino acid analogue.

In the present invention, the carrier peptide nucleic acid may comprise one or more gamma- or alpha-backbone-modified peptide nucleic acid monomers so as to be generally positively charged.

The gamma- or alpha-backbone-modified peptide nucleic acid monomers may comprise, in the backbone thereof, one or more positively charged amino acids selected from the group consisting of lysine (Lys, K), arginine (Arg, R), histidine (His, H), diamino butyric acid (DAB), ornithine (Orn), and an amino acid analogue, so as to be electrically positive.

In the present invention, modification of the peptide nucleic acid monomers to impart charges may be performed using nucleobase-modified peptide nucleic acid monomers besides the backbone modification. Preferably, the carrier peptide nucleic acid may comprise an amine, triazole or imidazole moiety in its nucleobase so as to be electrically positive, or may comprise carboxylic acid in its base so as to be electrically negative.

In the present invention, the modified nucleic acid monomers of the carrier peptide nucleic acid may further comprise negative charges in the backbone or nucleobase, but the modified peptide nucleic acid monomers preferably comprise a larger number of positively charged monomers than negatively charged monomers such that the carrier peptide nucleic acid is generally positively charged.

Preferably, the nucleic acid complex of Structural Formula (1) according to the present invention may be generally positively charged.

In the nucleic acid complex of Structural Formula (1) according to the present invention, at least one substance selected from the group consisting of a hydrophobic moiety, a hydrophilic moiety, a target antigen-specific antibody, an aptamer, and a fluorescent/luminescent marker may be bound to the bioactive nucleic acid and/or the carrier peptide nucleic acid. Preferably, one or more substances selected from the group consisting of the hydrophobic moiety, the hydrophilic moiety, the target antigen-specific antibody, the aptamer, and the fluorescent/luminescent marker for imaging may be bound to the carrier peptide nucleic acid.

In the present invention, the binding of at least one substance, selected from the group consisting of the hydrophobic moiety, the hydrophilic moiety, the target antigen-specific antibody, the aptamer, the quencher, the fluorescent marker, and the luminescent marker, to the bioactive nucleic acid and/or the carrier peptide nucleic acid, may be via a single covalent bond or a linker-mediated covalent bond, but is not limited thereto (see Table 1). Preferably, cell permeation-, solubility-, stability-, delivery- and imaging-related substances (e.g., hydrophobic moiety, etc.) bound to the nucleic acid carrier are present independently of the bioactive nucleic acid that regulates target gene expression.

In the present invention, as described above, complementary binding of the bioactive nucleic acid to the carrier peptide nucleic acid may largely be classified into antiparallel binding and parallel binding. The complementary binding is configured such that the bioactive nucleic acid is released in the presence of a sequence targeted by the bioactive nucleic acid, that is, a sequence complementary to the bioactive nucleic acid.

Antiparallel binding and parallel binding are determined according to 5'-directionality and 3'-directionality in DNA-DNA or DNA-PNA binding. Antiparallel binding is a general DNA-DNA or DNA-PNA binding method. Taking the nucleic acid complex of Structural Formula (1) according to the present invention as an example, antiparallel binding means that the bioactive nucleic acid in the 5' to 3' direction and the carrier peptide nucleic acid in the 3' to 5' direction are bound to each other. Parallel binding shows a somewhat lower binding affinity than antiparallel binding, and means that the bioactive nucleic acid and the carrier peptide nucleic acid are bound to each other in the 5' to 3' direction or the 3' to 5' direction.

In the nucleic acid complex of Structural Formula (1) according to the present invention, the binding affinity between the bioactive nucleic acid and the carrier peptide nucleic acid may preferably be lower than the binding affinity between the bioactive nucleic acid and a gene targeted by the bioactive nucleic acid, particularly the mRNA of the target gene. The binding affinity is determined by melting temperature (Tm).

As a specific example of a method for allowing the binding affinity (melting temperature (Tm)) between the bioactive nucleic acid and the carrier peptide nucleic acid to be lower than the binding affinity between the bioactive nucleic acid and a gene targeted by the bioactive nucleic acid, particularly the mRNA of the target gene, the bioactive nucleic acid and the carrier peptide nucleic acid may be bound to each other by parallel binding or partial specific binding, but the present invention is not limited thereto.

As another example, the carrier peptide nucleic acid may have at least one or more peptide nucleobase selected from the group consisting of a linker, a universal base, and a peptide nucleobase which has base not complementary to the corresponding base of the bioactive nucleic acid, but the present invention is not limited thereto (see Table 1).

The universal base used in the present invention may be one or more selected from the group consisting of inosine PNA, indole PNA, nitroindole PNA, and abasic PNA, which are bases that bind to natural bases, including adenine, guanine, cytosine, thymine, and uracil, without selectivity, and have lower binding affinity than complementary binding affinity. Preferably, inosine PNA may be used as the universal base.

TABLE 1

Examples of binding between bioactive nucleic acid and carrier peptide nucleic acid

| Type | Complex structure | | Features |
|---|---|---|---|
| I | Carrier peptide nucleic acid<br>Bioactive nucleic acid | 5'-[NNNNN*NNNNNNNNN*NNNNN]-3'<br>3'-[NNNNNNNNNNNNNNNNNNNNN]-5' | Partial match 1<br>(Substitution) |
| II | Carrier peptide nucleic acid<br>Bioactive nucleic acid | 5'-[NNNNNNNNNNNNNNNNNNNN]-3'<br>3'-[NNNNNNNNNNNNNNNNNNNNN]-5' | Partial match 2<br>(Insertion/Deletion) |
| III | Carrier peptide nucleic acid<br>Bioactive nucleic acid | 5'-[NNNNNNNSSSSNNSNNNNNNN]-3'<br>3'-[NNNNNNNNNNNNNNNNNNNNN]-5' | Universal base |
| IV | Carrier peptide nucleic acid<br>Bioactive nucleic acid | 5'-[NNNNNNNNNN=NNNNNNNNNN]-3'<br>3'-[NNNNNNNNNNNNNNNNNNNNN]-5' | Linker |
| V | Carrier peptide nucleic acid<br>Bioactive nucleic acid | 5'-[NNNNNNNNNNNNNNNNNNNNN]-3'<br>5'-[NNNNNNNNNNNNNNNNNNNNN]-3' | Parallel binding |

In Table 1 above, N represents nucleobases (ATGC); * represents a sequence which is not complementary to an antisense nucleic acid sequence; $ represents a universal base; = represents a linker; and 5'- and 3'- represent the directionalities of nucleic acid (bases).

The present invention provides a combination of binding form and electrical property of nucleic acids for regulating the function of the nucleic acid complex, may control the particle size and the time of action through the combination of binding form and electrical property of nucleic acids, and may increase cell permeability, solubility and specificity.

In the present invention, the time point at which the bioactive peptide nucleic acid binds to a target sequence in the presence of a target gene (the time of strand displacement of the bioactive nucleic acid to the target sequence, and the time of target specific release and binding of the bioactive nucleic acid) may be controlled by controlling the binding affinity between the carrier peptide nucleic acid and the bioactive peptide nucleic acid.

In the nucleic acid complex of Structural Formula (1) according to the present invention, the time of strand displacement of the bioactive nucleic acid to a target gene and the time of the target specific release and binding of the bioactive nucleic acid may be controlled by the non-specific bases of the carrier peptide nucleic acid for non-specific binding of the complex, the presence or absence of universal bases and a linker, and the number and position of the bases. In addition, these may also be controlled by a combination of these conditions with parallel or antiparallel binding which is complementary binding in the complex.

In the present invention, the particle size of the nucleic acid complex of Structural Formula (1) may be 5 nm to 300 nm, preferably 10 nm to 80 nm, most preferably 15 nm to 70 nm.

In the present invention, the particle size of the nucleic acid complex may be controlled by controlling the charge balance between the bioactive nucleic acid and the carrier peptide nucleic acid. Specifically, as the positive charges of the carrier peptide nucleic acid increase, the particle size becomes smaller, but if the positive charges of the carrier peptide nucleic acid exceed a certain level, the particle size becomes larger. In addition, the particle size of the nucleic acid complex is determined by proper charge balance between the bioactive nucleic acid and the carrier peptide nucleic acid depending on the charges of the bioactive peptide nucleic acid of the complex, which is another factor that determines the particle size.

The number of positive charges of the carrier peptide nucleic acid according to the present invention is 1 to 7 (indicating that 1 to 7 positively charged monomers are included), preferably 2 to 5, most preferably 2 to 3, and the net charge of charge balance of the bioactive nucleic acid is negative charge 0 to 5, preferably 0 to 3.

In the present invention, the nucleic acid complex of Structural Formula (1) may be produced by hybridization between the bioactive nucleic acid and the carrier peptide nucleic acid under proper conditions.

As used herein, the term "hybridization" means that complementary single-stranded nucleic acids form a double-stranded nucleic acid. Hybridization can occur when the complementarity between two nucleic acid strands is perfect (perfect match) or when some mismatched residues exist. The degree of complementarity necessary for hybridization may vary depending on hybridization conditions, particularly may be controlled by binding temperature.

In another aspect, the present invention is directed to a composition for diagnosing disease, the composition comprising the skin-penetrating carrier containing the nucleic acid complex having the structure of Structural Formula (1) or (2).

Preferably, when the skin-penetrating carrier according to the present invention is used for the purpose of diagnosing disease, a reporter and a quencher capable of quenching the fluorescence of the reporter may be bound to both ends of the bioactive nucleic acid or the carrier peptide nucleic acid. The reporter may be one or more selected from the group consisting of FAM (6-carboxyfluorescein), Texas red, HEX (2',4',5',7'-tetrachloro-6-carboxy-4,7-dichlorofluorescein), and Cy5. Preferably, Cy5 is used. The quencher may be one or more selected from the group consisting of TAMRA (6-carboxytetramethyl-rhodamine), BHQ1, BHQ2 and Dabcyl, but is not limited thereto.

In still another aspect, the present invention is directed to a composition for preventing or treating disease, the composition comprising the skin-penetrating carrier containing the nucleic acid complex having the structure of Structural Formula (1) or (2).

In yet another aspect, the present invention is directed to a method for preventing or treating disease, the method comprising administering, to a patient in need of prevention or treatment, the composition comprising the skin-penetrating carrier containing the nucleic acid complex having the structure of Structural Formula (1) or (2).

In still yet another aspect, the present invention is directed to the use of the skin-penetrating carrier containing the nucleic acid complex having the structure of Structural Formula (1) or (2), for preventing or treating disease.

In further another aspect, the present invention is directed to the use of the skin-penetrating carrier containing the nucleic acid complex having the structure of Structural Formula (1) or (2), in the manufacture of a medicament for preventing or treating disease.

As used herein, the term "target gene" refers to a nucleic acid sequence (nucleotide sequence) to be activated, inhibited or labeled, and is not different from and is used interchangeably with the term "target nucleic acid".

If the target nucleic acid (nucleotide sequence) comprising the target gene contacts (binds) the complex in vitro or in vivo, then the bioactive nucleic acid is separated from the carrier peptide nucleic acid and exhibits biological activity.

In the present invention, the disease that can be diagnosed, prevented or treated using the nucleic acid complex having the structure of Structural Formula (1) or (2) may be determined depending either on a target gene to which the bioactive nucleic acid in the nucleic acid complex binds, or on a therapeutic drug bound to the nucleic acid complex.

Preferably, the nucleic acid complex may be used for treatment of skin diseases, for example, psoriasis, atopic diseases including atopic dermatitis, skin cancer such as melanoma, keloid disease, diseases such as skin damage and pigmentation, tumors, cancer, inflammatory diseases, age-related macular degeneration, diabetic retinopathy, rare and severe diseases, cardiovascular diseases, metabolic diseases, and the like, but is not limited thereto.

Meanwhile, in the present invention, the term "composition for treatment" may be used interchangeably with "pharmaceutical composition". The composition for treatment comprises, as an active ingredient, the nucleic acid complex of the present invention, which comprises a bioactive nucleic acid and a carrier bioactive nucleic acid bound to the bioactive nucleic acid. In addition, the composition may further comprise a therapeutic drug for treating a target disease, which is bound to the nucleic acid complex.

Thus, in the present invention, the composition for treatment comprising the skin-penetrating carrier may be used for treatment of skin diseases, for example, psoriasis, atopic diseases including atopic dermatitis, skin cancer such as melanoma, keloid disease, diseases such as skin damage and pigmentation, tumors, cancer, inflammatory diseases, age-related macular degeneration, diabetic retinopathy, rare and severe diseases, cardiovascular diseases, metabolic diseases, and the like, but is not limited thereto.

The composition for treatment according to the present invention may be formulated in an oral or parenteral dosage form according to standard pharmaceutical practices. This formulation may contain additives such as a pharmacologically acceptable carrier, an excipient, a supplement, or a diluent besides the active ingredient.

Preferably, the composition for treatment according to the present invention may be formulated in the form of an aqueous solution, gel, ointment, cream, lotion, paste, liniment or patch.

Most preferably, the composition may be formulated in the form of aqueous solution. In this case, the aqueous solution may take the form of distilled water or a buffered solution.

The term "physiologically acceptable" refers to not abrogating the biological activity and properties of the compound.

The term "carrier" is defined as a compound which facilitates the addition of the complex into cells or tissue. For example, dimethylsulfoxide (DMSO) is a carrier which is commonly used to facilitate the penetration of a number of organic compounds into the cells or tissue of an organism.

The term "diluent" is defined as a compound that not only stabilizes the biologically active form of the target compound, but also a compound that is diluted in water in which it was dissolved. Salts dissolved in buffer solution are used as diluents in the related art. A commonly used buffer solution is phosphate buffered saline, which mimics the concentrations of salts in the human body. Since the buffer salts can control the pH of solution at low concentration, biological activity of compounds is rarely altered by buffer diluents.

The substance containing the nucleic acid complex used herein can be administered to a human patient per se, or in pharmaceutical compositions where they are mixed with other active ingredients, as in combination therapy, or suitable carriers or excipients.

Pharmaceutical compositions suitable for use in the present invention include compositions where the active ingredients are contained in an amount effective to achieve intended purposes. More specifically, a therapeutically effective amount means an amount of a compound effective to prevent, stabilize, alleviate or ameliorate symptoms of disease, or prolong the survival of the subject being treated. Determination of a therapeutically effective amount is well within the capability of those skilled in the art, especially in light of the detailed disclosure provided herein.

As used herein, the term "preventing" or "prevention" refers to all actions that exhibit anticancer activity and inhibit the growth of cancer or delay the development of cancer by administering (or applying) a pharmaceutical composition comprising the complex or a pharmaceutically acceptable salt thereof.

As used herein, the term "treating" or "treatment" refers to all actions that alleviate or perfectly cure cancer by administering (or applying) a pharmaceutical composition comprising the complex or a pharmaceutically acceptable salt thereof.

In the present invention, the composition for preventing or treating disease comprising the skin-penetrating carrier may preferably be a composition for preventing or treating skin disease. A target gene, to which the bioactive nucleic acid contained in the nucleic acid complex binds, may be, for example, any one or more selected from the group consisting of IFI16, TGFβR2, TLR2, smad3 and TIEG1, but is not limited thereto. Examples of the skin disease include, but is not limited to, psoriasis, skin cancer, atopic disease, keloid disease, and pigmentation.

Preferably, the present invention provides a composition for treating psoriasis. The composition for treating psoriasis according to the present invention comprises: an IFI16-specific bioactive peptide nucleic acid represented by SEQ ID NO: 22; and a carrier peptide nucleic acid complementary thereto. The carrier peptide nucleic acid may preferably have the sequence of SEQ ID NO: 23 or SEQ ID NO: 24, and a portion of the sequence may also be substituted with universal bases.

The present invention provides a composition for treating malignant melanoma. The composition for treating malignant melanoma according to the present invention comprises: a TGFRβ2-specific bioactive nucleic acid having the sequence of SEQ ID NO: 25 or SEQ ID NO: 26; and a carrier peptide nucleic acid complementary thereto. The carrier peptide nucleic acid may preferably have the sequence of any one of SEQ ID NO: 27 to SEQ ID NO: 30, and a portion of the sequence may also be substituted with universal bases.

The present invention provides a composition for treating atopic dermatitis. The composition for treating atopic dermatitis according to the present invention comprises: a TLR2-specific bioactive nucleic acid having the sequence of SEQ ID NO: 31 or SEQ ID NO: 32; and a carrier peptide nucleic acid complementary thereto. The carrier peptide nucleic acid may preferably have the sequence of any one of SEQ ID NO: 33 to SEQ ID NO: 35, and a portion of the sequence may also be substituted with universal bases.

The present invention also provides a composition for treating skin damage. The composition for treating skin damage is for skin regeneration including skin wound healing, but is not limited thereto. The composition for treating skin damage according to the present invention comprises: a Smad3-specific bioactive peptide nucleic acid having the sequence of SEQ ID NO: 36 or SEQ ID NO: 37; and a carrier peptide nucleic acid complementary thereto. The carrier peptide nucleic acid may preferably have the sequence of any one of SEQ ID NOs: 38 to SEQ ID NO: 41, and a portion of the sequence may also be substituted with universal bases.

The present invention provides a composition for treating keloids. The composition for treating keloids according to the present invention comprises: a TIEG1-specific bioactive nucleic acid having the sequence of SEQ ID NO: 42 or SEQ ID NO: 43; and a carrier peptide nucleic acid complementary thereto. The carrier peptide nucleic acid may preferably have the sequence of any one of SEQ ID NO: 44 to SEQ ID NO: 47, and a portion of the sequence may also be substituted with universal bases.

In the present invention, the nucleic acid complex contained in the skin-penetrating carrier may be administered (or applied) via a carrier such as a liposome. The liposome may aid in targeting the complex toward a specific tissue, such as lymphoid tissue, or specifically targeting the complex toward infected cells, and may also help to increase the half-life of the composition comprising the complex. Examples of the liposome include emulsions, foams, micelles, insoluble monolayers, liquid crystals, phospholipid dispersions, lamellar layers, and the like. In these preparations, the complex to be delivered is incorporated as part of a liposome, alone or in conjunction with a molecule which binds to, e.g., a receptor prevalent among lymphoid cells, such as monoclonal antibodies which bind to the CD45 antigen, or with other therapeutic compositions. Thus, liposomes either filled or decorated with a desired complex of the present invention can be directed to the site of lymphoid cells.

Liposomes for use in the present invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes. For example, methods as disclosed in literature [Szoka, et al., Ann. Rev. Biophys. Bioeng., 9:467, 1980, and U.S. Pat. Nos. 4,235,871, 4,501,728, 4,837,028, and 5,019,369] can be used.

In another aspect, the present invention provides a method of treating and suppressing (or alleviating) disease by administering (or applying), to a subject, the skin-penetrating carrier containing the nucleic acid complex having the structure of Structural Formula (1) or (2).

A disease that can be treated using the carrier of the present invention is determined according to the characteristics of the bioactive nucleic acid used, and is not particularly limited.

The composition comprising the carrier according to the present invention may be applied to the skin in a pharmaceutically effective amount in order to treat the diseases or suppress (or alleviate) the diseases symptoms. The dose/application amount of the pharmaceutical composition of the present invention may vary depending on various factors such as the kind of skin diseases, the patient's age and body weight, the characteristics and degree of symptoms, the kind of current treatment method, the frequency of treatment, the mode and route of administration (application), and the like, and may be easily determined by those of ordinary skill in the related art. The composition of the present invention may be administered (applied) together with the pharmacological or physiological ingredient, or sequentially administered (applied). In addition, the composition of the present invention may also be administered (applied) in combination with conventional additional therapeutic agents, and sequentially or simultaneously with the conventional therapeutic agent. The administration (application) may be single dose administration (application) or multi-dose administration (application).

In the present invention, the term "subject" refers to a mammal suffering from a condition or disease which can be alleviated, suppressed or treated by administering (applying) the skin-penetrating carrier of the present invention, or being at risk of developing this condition or disease. Preferably, it refers to a human being.

In addition, the dose (application amount) of the compound of the present invention to the human body may vary depending on the patient's age, body weight and gender, the mode of administration (application), the patient's health condition, and the severity of the disease. Based on an adult patient weighing 70 kg, the dose is generally 0.001 to 1,000 mg/day, preferably 0.01 to 500 mg/day. Depending on the judgment of a doctor or a pharmacist, the dose may be administered (applied) once or several times a day at predetermined time intervals.

Toxicity and therapeutic efficacy of the skin-penetrating carrier described herein or a composition comprising the same can be determined by standard pharmaceutical procedures in cell cultures or experimental animals, e.g., by determining the $LD_{50}$ (the dose lethal to 50% of the population) and the $ED_{50}$ (the dose therapeutically effective in 50% of the population). The dose ratio between therapeutic and toxic effects is the therapeutic index and it can be expressed as the ratio $ED_{50}$ (or $IC_{50}$)/$LD_{50}$. Compounds that exhibit large therapeutic indices are preferred. The data obtained from these cell culture assays can be used in formulating a range of doses for use in humans. The dosages or application amounts of these compounds lay preferably within a range of circulating concentrations that include the $ED_{50}$ (or $IC_{50}$) with little or no toxicity.

Hereinafter, the present invention will be described in more detail with reference to examples. It will be obvious to those skilled in the art that these examples are merely to illustrate the present invention, and the scope of the present invention is not limited by these examples.

Example 1: Bioactive Nucleic Acid, Carrier Peptide Nucleic Acid, and Production of Complex Using the Same To verify the skin penetration effect and skin retention effect of the nucleic acid complex of Structural Formula (1) according to the present invention, IFI16, a psoriasis disease-targeting gene, was used as a target gene. IFI16 is a protein that is commonly expressed in the skin of patients with psoriasis, and is considered an important target in the treatment of psoriasis (Up-regulation of Interferon-inducible protein 16 contributes to psoriasis by modulating chemokine production in keratinocytes 6:25381).

To evaluate the skin penetration effect and skin retention effect of the nucleic acid complex, antisense peptide nucleic acid (PNA) and RNA were used as bioactive nucleic acids against IFI16.

The bioactive nucleic acid (antisense PNA and RNA) of the present invention have the sequences set forth in SEQ ID NOs: 1 to 9. The peptide nucleic acid-based bioactive nucleic acids used in this Example were labeled with Cy3 for imaging at the 3' end, and the nucleotide sequences, monomer modifications and structures thereof are shown in Table 2 below.

All the peptide nucleic acids used in the present invention were synthesized using an HPLC purification method by PANAGENE (Korea). Carrier peptide nucleic acids used in the Example of the present invention have the sequences set forth in SEQ ID NOs: 10 to 21 (Table 2).

To impart electrical properties, the modification of the monomer in which a peptide nucleic acid backbone modified to be positively charged using lysine (Lys, K; indicated by $^{(+)}$) and a peptide backbone modified to be negatively charged using glutamic acid (Glu, E; indicated by $^{(-)}$) were constructed.

Each bioactive nucleic acid and carrier peptide nucleic acid were hybridized in DMSC, and as a result, complexes, each comprising the bioactive nucleic acid and the carrier peptide nucleic acid, were synthesized.

Example 2: Analysis of Skin Penetration Effect of Nucleic Acid Complex Comprising Bioactive Nucleic Acid and Carrier Peptide Nucleic Acid To analyze the skin penetration effect of the complexes produced in Example 1, a predetermined amount of each complex was applied to the back of nude mice which were then left to stand for 1, 3 and 24 hours, and the tissue of the applied area was biopsied. The biopsied tissue was fixed in 4% formalin solution, left to stand for one day, sectioned to 20 μm using a microtome, and mounted on a glass slide. The mounted tissue was observed by a fluorescence microscope to examine whether the complex penetrated the skin.

The nucleic acid complexes used in this Example are shown in Table 3 below.

TABLE 2

Sequences of bioactive nucleic acids and carrier peptide nucleic acids for verification of skin penetration and skin retention effects

| Component | SEQ ID NO | Nucleotide sequence | Monomer modification |
|---|---|---|---|
| Bioactive nucleic acid | SEQ ID NO: 1 | 5'-AT$^{(-)}$TCA$^{(+)}$CAT$^{(-)}$CAG$^{(+)}$CC$^{(-)}$AC-O-K(cy3)-3' | -+-+- |
|  | SEQ ID NO: 2 | 5'-ATTCACATCAG)CCAC-O-K(cy3)-3' |  |
|  | SEQ ID NO: 3 | 5'-AT$^{(-)}$TCAC$^{(+)}$ATCAG$^{(-)}$CCAC-O-K(cy3)-3' | -+- |
|  | SEQ ID NO: 4 | 5'-AT$^{(-)}$TCA$^{(-)}$CAT$^{(-)}$CAG$^{(-)}$CC$^{(-)}$AC-O-K(cy3)-3' | ----- |
|  | SEQ ID NO: 5 | 5'-AT$^{(-)}$TCACAT$^{(-)}$CAGCC$^{(-)}$AC-O-K(cy3)-3' | --- |
|  | SEQ ID NO: 6 | 5'-ATT$^{(+)}$CACATC$^{(+)}$AGCC$^{(+)}$AC-O-K(cy3)-3' | ++ |
|  | SEQ ID NO: 7 | 5'-A$^{(+)}$TTC$^{(+)}$AC$^{(+)}$ATC$^{(+)}$AGCC$^{(+)}$AC-O-K(cy3)-3' | +++++ |
|  | SEQ ID NO: 8 | 5'-ATTCACATCAG)CCAC-(cy3)-3' |  |
|  | SEQ ID NO: 9 | 5'-stearic acid-O-AT$^{(-)}$TCA$^{(+)}$CAT$^{(-)}$CAG$^{(+)}$CC$^{(-)}$AC-O-K(cy3)-3' | -+-+- |
| Carrier peptide nucleic acid | SEQ ID NO: 10 | GTGGCGATGTGAAT |  |
|  | SEQ ID NO: 11 | 5'-TAAGTGTAGTCGGTG-O-K-3' |  |
|  | SEQ ID NO: 12 | 5'-TA$^{(+)}$AGTGTAGTCGG$^{(+)}$TG-O-K-3' | ++ |
|  | SEQ ID NO: 13 | 5'-TA$^{(+)}$AGTGTA$^{(+)}$GTCGG$^{(+)}$TG-O-K-3' | +++ |
|  | SEQ ID NO: 14 | 5'-TA$^{(+)}$AGT$^{(+)}$GTA$^{(+)}$GTC$^{(+)}$GG$^{(+)}$TG-O-K-3' | +++++ |
|  | SEQ ID NO: 15 | 5'-TA$^{(-)}$AGTGTA$^{(-)}$GTCGG$^{(-)}$TG-O-K-3' | --- |
|  | SEQ ID NO: 16 | 5'-TA$^{(-)}$AGT$^{(-)}$GTA$^{(-)}$GTC$^{(-)}$GG$^{(-)}$TG-O-K-3' | ----- |
|  | SEQ ID NO: 17 | 5'-CG$^{(+)}$GT$^{(+)}$G-O-K-3' | ++ |
|  | SEQ ID NO: 18 | 5'-GTC$^{(+)}$GGT$^{(+)}$G-O-K-3' | ++ |
|  | SEQ ID NO: 19 | 5'-TAG$^{(+)}$TCG$^{(+)}$GTG-O-K-3 | ++ |
|  | SEQ ID NO: 20 | 5'-TG$^{+}$TAG$^{(+)}$TCGG$^{(+)}$TG-O-K-3' | +++ |
|  | SEQ ID NO: 21 | 5'-AG$^{(+)}$TGTA$^{(+)}$GTCG$^{(+)}$GTG-O-K-3' | +++ |

TABLE 3

Nucleic acid complexes for analysis of skin penetration effect

| Name | Nucleic acid complex |
| --- | --- |
| siRNA single | SEQ ID NO: 8 |
| siRNA duplex | SEQ ID NOs: 8 and 10 |
| PNA single | SEQ ID NO: 1 |
| PNA duplex 1 | SEQ ID NOs: 1 and 17 |
| PNA duplex 2 | SEQ ID NOs: 1 and 13 |

As a result, as shown in FIG. 3 and FIGS. 4a to 4l, it was confirmed that various nucleic acid complexes exhibited transdermal delivery effects at 1, 3 and 24 hours.

Example 3: Analysis of Skin Penetration Effect of Skin-Penetrating Carrier which Contains Complex Having Structure of Structural Formula (1) to which Low-Molecular-Weight Substance is Hound Via Linker To analyze the skin penetration effect of a skin-penetrating carrier in which a low-molecular-weight substance is bound to each complex via a linker, in comparison with each complex produced in Example 1, a predetermined amount of each complex was applied to the back of nude mice which were then left to stand for 0, 3 and 24 hours, and the tissue of the applied area was biopsied. The biopsied tissue was fixed in 4% formalin solution, left to stand for one day, sectioned to 20 μm using a microtome, and mounted on a glass slide. The mounted tissue was observed by a fluorescence microscope to examine the transdermal delivery effect of the skin-penetrating carrier in which the low-molecular-weight substance is bound to each nucleic acid complex.

The nucleic acid complexes used in this Example are shown in Table 4 below.

TABLE 4

Nucleic acid complexes for analysis of skin penetration effect of nucleic acid complexes having low-molecular-weight substance bound thereto

| Name | Nucleic acid complex |
| --- | --- |
| PNA duplex 1 | SEQ ID NOs: 1 and 17 |
| PNA duplex 2 | SEQ ID NOs: 1 and 13 |
| PNA duplex 3 | SEQ ID NOs: 9 and 17 |
| PNA duplex 4 | SEQ ID NOs: 9 and 13 |

As a result, as shown in FIGS. 5a to 5c, it was confirmed through the fluorescence microscope that the skin-penetrating nucleic acid complexes having the low-molecular-weight substance bound thereto via the linker also exhibited a transdermal delivery effect at and after 3 hours.

Example 4: Analysis of Psoriasis Treatment Effect of Skin-Penetrating Carrier Containing Complex Having Structure of Structural Formula (1)

Skin-penetrating carriers, each comprising an IFI16 gene-targeting bioactive peptide nucleic acid and a carrier peptide nucleic acid, were produced to have the structures shown in Table 5 below according to Example 1, and the psoriasis treatment effect thereof was analyzed.

TABLE 5

Sequences of bioactive peptide nucleic acid and carrier peptide nucleic acid for inhibiting IFI16 activity

| Component | SEQ ID NO | Nucleotide sequence | Monomer modification |
| --- | --- | --- | --- |
| Bioactive nucleic acid | SEQ ID NO: 22 | 5'-AT$^{(-)}$TCA$^{(+)}$CAT$^{(-)}$CAG$^{(+)}$CC$^{(-)}$AC-O-K-3' | -+-+- |
| Carrier peptide nucleic acid | SEQ ID NO: 23 | 5'-CG$^{(+)}$GT$^{(+)}$G-O-K-3' | ++ |
|  | SEQ ID NO: 24 | 5'-K-O-GT$^{(+)}$GG$^{(+)}$C-3' | ++ |

Example 4-1: Cell Culture

Human keratinocytes (HaCaT) obtained from the CLS (CLS Cell Lines Service, Germany) were cultured in DMEM culture medium (Dulbecco Modified Eagle Medium, Welgene, Korea) containing 10% (v/v) fetal bovine serum, 100 units/ml penicillin and 100 μg/ml streptomycin at 37° C. under 5% (v/v) $CO_2$. To prepare a psoriasis-mimicking cell model, the cells were treated with 10 ng/mL IL-17A and cultured.

Example 4-2: Analysis of Cell Viability in Keratinocytes by MTT Assay

The complexes having the structures shown in Table 5, each comprising the bioactive nucleic acid and the carrier peptide nucleic acid were produced according to Example 1. Human keratinocytes were seeded into a 96-well plate at a density of 6×10³ cells/well, treated with the complex, and then cultured for 24 hours under the conditions shown in Example 4-1. Then, each well was treated with 20 μL of MTT (3-(4,5-dimethylthiazol-2-yl)-2,5-diphenyltetrazolium bromide) solution prepared at a concentration of 5 mg/mL in 1×PBS. Next, each well was incubated for 4 hours, and then optical density (OD) was measured by a spectrophotometer and analyzed.

Figure 6A:
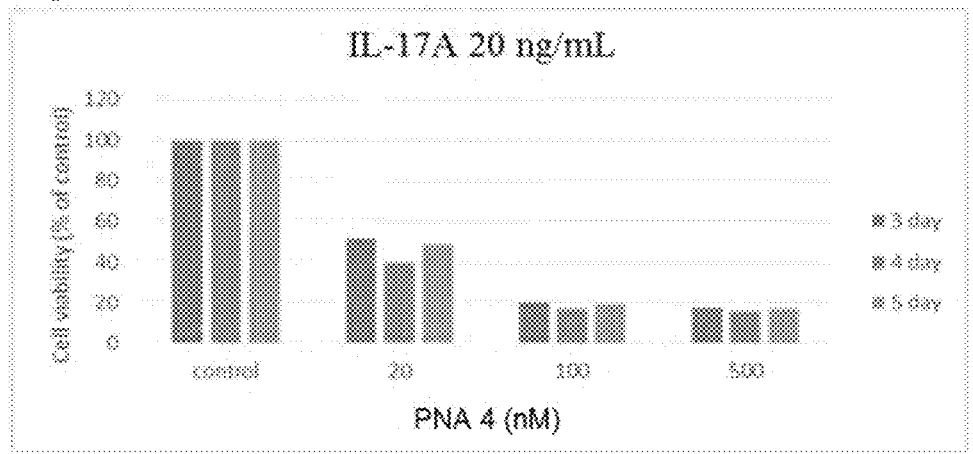

The nucleic acid complex of SEQ ID NO: 22 and SEQ ID NO: 23 (PNA 4) was used. As a result, as shown in FIG. 6a, it was confirmed that the cell viability in the psoriasis-mimicking cell model induced by IL-17A was decreased by the nucleic acid complex in a concentration-dependent manner.

Example 4-3: Analysis of Gene Expression by Western Blot Assay

Human keratinocytes were seeded into a 6-well plate at a density of 1×10⁵ cells/well, cultured for 24 hours under the conditions shown in Example 4-1, treated with the complex comprising the bioactive nucleic acid and the carrier peptide nucleic acid, and then cultured for 24, 48 and 72 hours. Next, 30 μL of RIPA buffer was added to each well to obtain a protein lysate. The protein lysate was quantified using the BCA assay kit (Thermo Fisher, USA), and 30 μg of the protein was separated by size through electrophoresis, transferred to a PVDF membrane, and then treated with IFI16 (Cell Signaling Technology, USA) and p-NFkB (Cell Signaling Technology, USA) as primary antibodies at a dilution of 1:1000, and then left to stand at 4° C. for one day. Next, the membrane was washed with 1×TBS-T, treated with Goat Anti-Rabbit (SantaCruz Biotech., USA) as secondary antibody at a dilution of 1:2000, and left to stand at room temperature for 2 hours. The membrane was treated with Supersignal™ West Femto Maximum Sensitivity Substrate (Thermo Fisher, USA), and the efficiency of inhibition of the target gene expression in the keratinocytes was analyzed using an Image 600 (Amersham, Germany) imager.

Figure 6B:
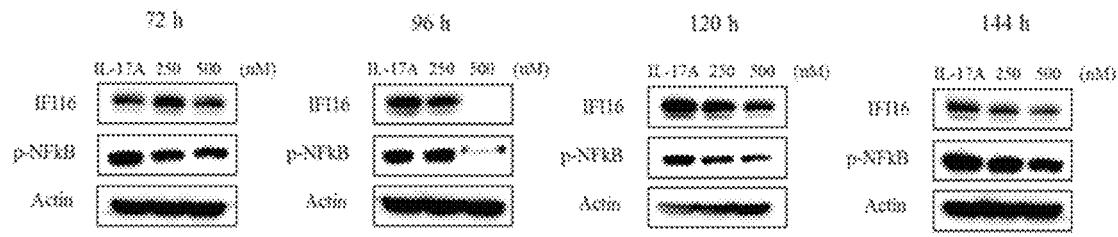

For the nucleic acid complex of SEQ ID NO: 22 and SEQ ID NO: 23 shown in Table 5, the expression patterns of IFI16 and downstream genes thereof were analyzed. As a result, as shown in FIG. 6b, it was confirmed that expression of the target gene and downstream genes thereof was inhibited by the nucleic acid complex in a concentration-dependent manner with time.

Example 4-4: Analysis of Psoriasis Phenotype in Imiquimod-Induced Psoriasis Animal Model A psoriasis-induced animal model was prepared by applying 62.5 mg of 5% imiquimod to the right ear of Balb/C mice daily for 7 days. For the nucleic acid complex of SEQ ID NO: 22 and SEQ ID NO: 23 shown in Table 5, the psoriasis phenotype in the animal model was analyzed in images and the ear thickness was measured in micrometers.

Figure 6C:
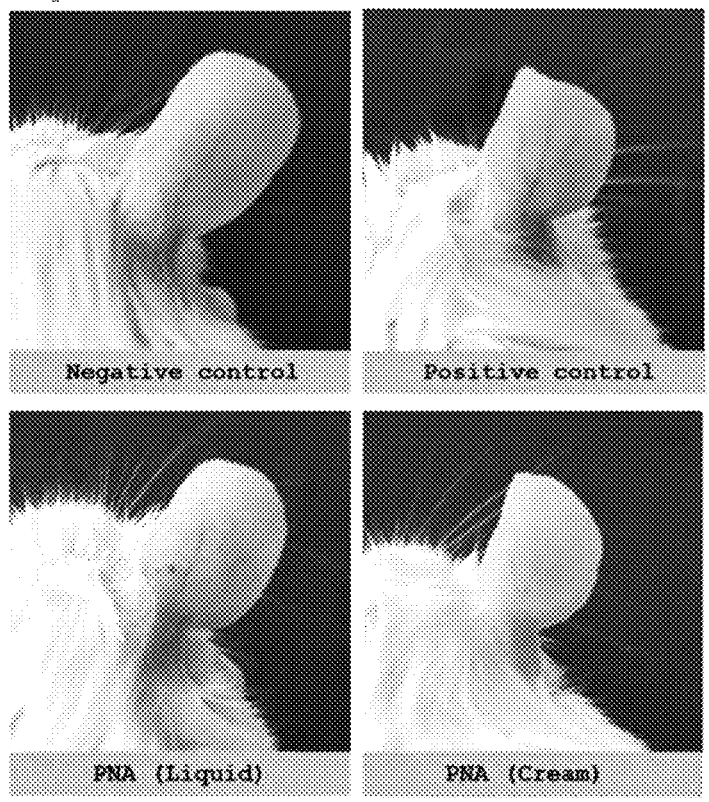
Figure 6D:
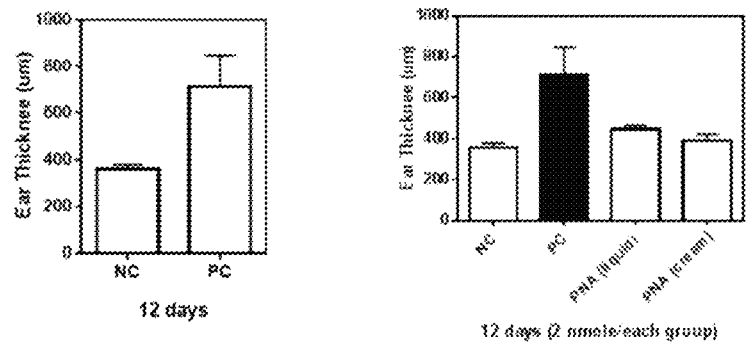
Figure 6D:
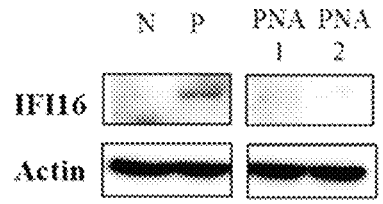

As a result, it was confirmed that the psoriasis phenotype decreased in the nucleic acid complex group (FIG. 6c). In addition, it could be confirmed that the ear thickness decreased in the nucleic acid complex-applied group compared to the psoriasis-induced animal group (FIG. 6d; PNA 1 is a nucleic acid complex comprising no formulation, and PNA 2 is a nucleic acid complex comprising a cream formulation).

Example 4-5: Analysis of Phenotype in Psoriasis-Induced Animal Model by H&E Staining On the last day of the experiment performed under the conditions of Example 4-4, the mouse ear tissue was biopsied and fixed in 4% formalin solution for one day. The fixed tissue was embedded in paraffin, sectioned to 5 μm, and mounted on slide glass. The mounted tissue was stained with Hematoxylin:Eoin staining solution for a predetermined time, washed with 1×PBS, and then analyzed with a microscope.

Figure 6E:
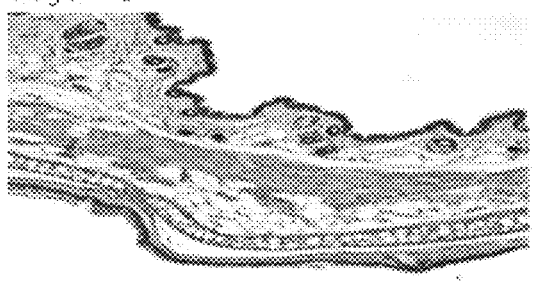
Figure 6E:
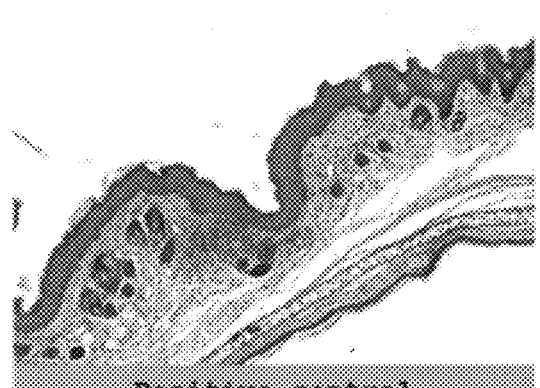
Figure 6E:
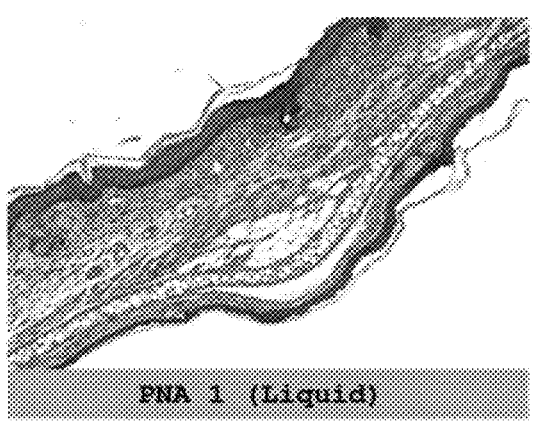
Figure 6E:
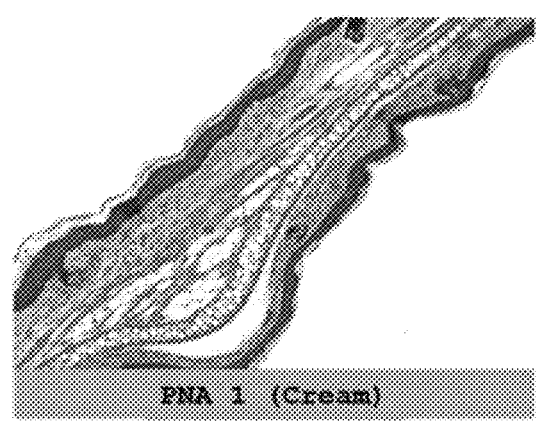

As a result, as shown in FIG. 6e, abnormal growth of epidermis in the group treated with the nucleic acid complex decreased compared to that in the psoriasis-derived control group.

Example 4-6: Analysis of Inflammatory Marker in Tissue of Psoriasis-Induced Animal Model by Immunostaining On the last day of the animal experiment performed under the conditions of Example 4-4, the mouse ear tissue was biopsied and fixed in 4% formalin solution for one day. The fixed tissue was embedded in paraffin, sectioned to 5 μm, and mounted on a glass slide. The mounted tissue was blocked in 0.5% BSA solution for 1 hour, treated with primary antibody solution against CD3 and CD11c, and incubated for one day. Next, the primary antibody solution was removed, and the remaining material was washed with 1×PBS, treated with secondary antibody solution, incubated at room temperature for 2 hours, and then analyzed by DAB straining.

Figure 6F:
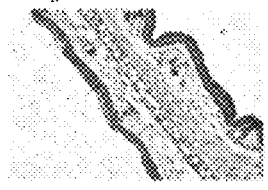
Figure 6F:
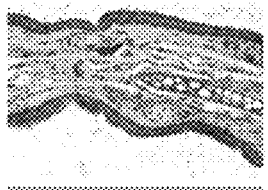
Figure 6F:
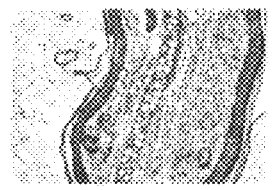
Figure 6F:
Figure 6F:
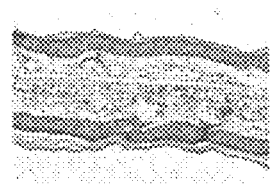
Figure 6F:
Figure 6F:
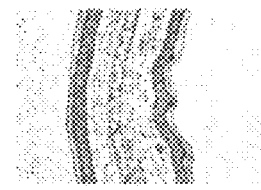
Figure 6F:
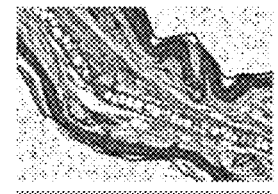

As a result, as shown in FIG. 6f, it was confirmed that the inflammatory markers CD3 and CD11c in the tissue decreased in the group treated with the nucleic acid complex compared to the psoriasis-induced control group.

Example 5: Analysis of Malignant Melanoma Treatment Effect of Skin-Penetrating Carrier Containing Complex Having Structure of Structural Formula (1)

To analyze the malignant melanoma treatment effect of the nucleic acid complex, TGFβR2 was used as a target gene. Since the development of an RNA-based therapeutic agent that inhibits the TGFβ-2-induced activation mechanism among cancer metastasis mechanisms, an experiment was performed to verify the therapeutic effect of the nucleic acid complex.

TABLE 6

Sequences of bioactive nucleic acid and carrier peptide nucleic acid for inhibiting TGFβR2 activity

| Component | SEQ ID NO | Nucleotide sequence | Monomer modification |
|---|---|---|---|
| Bioactive nucleic acid | SEQ ID NO: 25 | 5'-G⁽⁻⁾GTC⁽⁺⁾ATC⁽⁻⁾CAC⁽⁺⁾AGA⁽⁻⁾CA-O-K-3' | -+-+- |
| | SEQ ID NO: 26 | 5'-GA⁽⁻⁾CAA⁽⁺⁾TGA⁽⁻⁾TAG⁽⁺⁾TAT⁽⁻⁾T-O-K-3' | -+-+- |
| Carrier peptide nucleic acid | SEQ ID NO: 27 | 5'-K-O-AA⁽⁺⁾TA⁽⁺⁾C-3' | ++ |
| | SEQ ID NO: 28 | 5'-TG⁽⁺⁾TCTGTG⁽⁺⁾GATGAC⁽⁺⁾C-O-K-3' | +++ |
| | SEQ ID NO: 29 | 5'-CT⁽⁺⁾GTTACT⁽⁺⁾ATCATA⁽⁺⁾A-O-K-3' | +++ |
| | SEQ ID NO: 30 | 5'-A⁽⁺⁾ATACTA⁽⁺⁾TCATTG⁽⁺⁾TC-O-K-3' | +++ |

Example 5-1: Cell Culture

Metastatic skin melanoma cells (A375SM) obtained from the ATCC (American Type Culture Collection, USA) were cultured in DMEM culture medium (Dulbecco Modified Eagle Medium, Welgene, Korea) containing 10% (v/v) fetal bovine serum, 100 units/ml penicillin and 100 μg/ml streptomycin at 37° C. under 5% (v/v) $CO_2$. To analyze metastasis, the cells were treated with 5 ng/mL TGFβ-2 and incubated.

Example 5-2: Analysis of Gene Expression by Western Blot Assay

Metastatic skin melanoma cells were seeded into a 6-well plate at a density of $1 \times 10^5$ cells/well, cultured for 24 hours under the conditions shown in Example 5-1, treated with the complex comprising the bioactive nucleic acid and the carrier peptide nucleic acid, and then cultured for 24, 48 and 72 hours. Next, 30 μL of RIPA buffer was added to each well to obtain a protein lysate. The protein lysate was quantified using the BCA assay kit (Thermo Fisher, USA), and 30 μg of the protein was separated by size through electrophoresis, transferred to a PVDF membrane, and then treated with TGFβR2 (Abcam, USA), MMP9 (SantaCruz Biotech., USA) and p-Akt1 (Cell Signaling Technology, USA) as primary antibodies at a dilution of 1:1000, and then left to stand at 4° C. for one day. Next, the membrane was washed with 1×TBS-T, treated with Goat Anti-Rabbit, Goat Anti-mouse (SantaCruz Biotech., USA) as secondary antibody at a dilution of 1:2000, and left to stand at room temperature for 2 hours. The membrane was treated with Supersignal™ West Femto Maximum Sensitivity Substrate (Thermo Fisher, USA), and the efficiency of inhibition of the target gene expression in the metastatic skin melanoma cells was analyzed using an Image 600 (Amersham, Germany) imager.

The expression patterns of TGFβR2 and downstream genes thereof in the metastatic skin melanoma cells were analyzed. The nucleic acid complexes used in this Example are shown in Table 7.

TABLE 7

| No. | Nucleic acid complex |
|---|---|
| 1 | SEQ ID NOs: 25 and 27 |
| 2 | SEQ ID NOs: 25 and 28 |
| 3 | SEQ ID NOs: 26 and 29 |
| 4 | SEQ ID NOs: 26 and 30 |

Nucleic acid complexes for analysis of TGFβR2 expression in melanoma cells

As a result, as shown in FIG. 7a, it was confirmed that expression of the target gene and downstream genes thereof was inhibited by the nucleic acid complex in a concentration-dependent manner with time.

Example 5-3: Analysis of Cell Migration Inhibitory Effect of Nucleic Acid Complex by Cell Migration Assay Metastatic skin melanoma cells were seeded into the upper chamber of a 24-well plate at a density of $2 \times 10^4$ cells/well, and all the chambers were treated with FBS-free medium. The cells were cultured for 24 hours under the conditions described in Example 5-1, and the upper chamber was treated with the complex comprising the bioactive peptide nucleic acid and the carrier peptide nucleic, and the lower chamber was treated with 20 ng/mL TGFβ-2, followed by culture for 24, 48 and 72 hours. Then, for analysis of cell migration, the cells were stained with 0.5% crystal violet. The stained cells were treated with methanol to dissolve the crystal violet, and then the absorbance at 450 nm was measured.

For the nucleic acid complexes shown in Table 7 above, the cell migration inhibitory effect of each complex in the metastatic cell melanoma cells was analyzed. As a result, as shown in FIG. 7b, it was confirmed that cell migration was inhibited by the nucleic acid complex with time.

Example 6: Analysis of Atopic Dermatitis Treatment Effect of Skin-Penetrating Carrier Containing Complex Having Structure of Structural Formula (1)

To analyze the atopic dermatitis treatment effect of the nucleic acid complex, TLR2 (Toll-Like Receptor 2) was used as a target gene. TLR2 is a gene that is expressed when allergens or bacteria penetrate the skin. TLR2 is overexpressed in atopic dermatitis patients, and exacerbates atopic dermatitis due to increased inflammation caused by inflammatory cytokines in the skin. For this reason, TLR2 is considered an important target in atopic dermatitis.

TABLE 8

Sequences of bioactive nucleic acid and carrier peptide nucleic acid for inhibiting TLR2

| Component | SEQ ID NO | Nucleotide sequence | Monomer modification |
|---|---|---|---|
| Bioactive nucleic acid | SEQ ID NO: 31 | 5'-A$^{(-)}$TGT$^{(-)}$AGG$^{(-)}$TG$^{(+)}$ATCC$^{(-)}$TGTT-O-K-3' | -+-+- |
|  | SEQ ID NO: 32 | GLFDIIKKIAESF-O-A$^{(-)}$TGT$^{(-)}$AGG$^{(-)}$TG$^{(+)}$ATCC$^{(-)}$TGTT-O-K | -+-+- |
| Carrier peptide nucleic acid | SEQ ID NO: 33 | 5'-K-O-A$^{(+)}$AC$^{(+)}$AG-3 | ++ |
|  | SEQ ID NO: 34 | 5'-K-O-A$^{(+)}$AC$^{(+)}$AG-O-Histidine(10)-3' | ++ |
|  | SEQ ID NO: 35 | K-O-T$^{(+)}$ACAGGA$^{(+)}$TCACCT$^{(+)}$ACAT-O-Histidine(10) | +++ |

Example 6-1: Cell Culture

Human keratinocytes (HaCaT) obtained from the CLS (CLS Cell Lines Service, Germany) were cultured in DMEM culture medium (Dulbecco Modified Eagle Medium, Welgene, Korea) containing 10% (v/v) fetal bovine serum, 100 units/ml penicillin and 100 μg/ml streptomycin at 37° C. under 5% (v/v) $CO_2$. To prepare an atopic dermatitis mimicking cell model, the cells were treated with 5 ng/mL house dust mite extract and 5 μM DNCB (2-dinitrochlorobenzene) and cultured for 24 hours.

Example 6-2: Analysis of Cell Viability in Keratinocytes by MTT Assay

Human keratinocytes were seeded into a 96-well plate at a density of 6×10³ cells/well, cultured for 24 hours under the conditions described in Example 6-1, and then treated with the complexes produced to have the structure shown in Table 8, each comprising the bioactive nucleic acid and the carrier peptide nucleic acid. Next, each well was treated with 20 μL of MTT (3-(4,5-dimethylthiazol-2-yl)-2,5-diphenyltetrazolium bromide) solution prepared at a concentration of 5 mg/mL in 1×PBS. Next, each well was incubated for 4 hours, and then the optical density (OD) was measured by a spectrophotometer and analyzed.

Figure 8A:
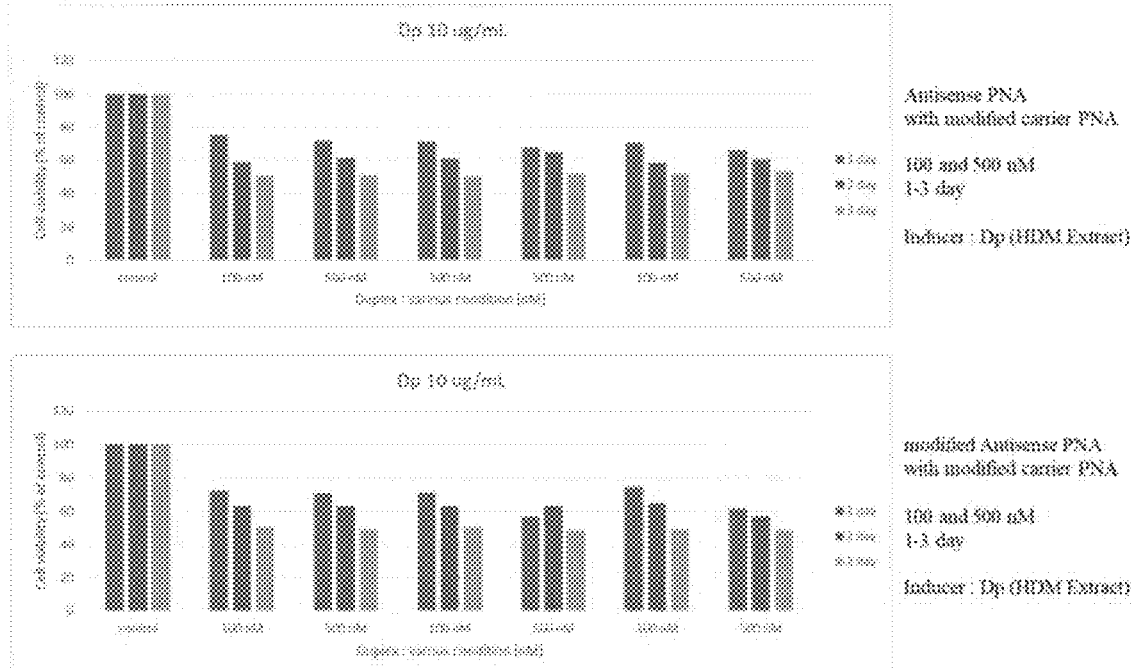

As a result, as shown in FIG. 8a, it was confirmed that the cell viability in the atopic dermatitis mimicking cell model induced by house dust mite extract or DNCB was decreased by the nucleic acid complex in a concentration-dependent manner.

Example 6-3: Analysis of Gene Expression by Western Blot Assay

Human keratinocytes were seeded into a 6-well plate at a density of 1×10⁵ cells/well, cultured for 24 hours under the conditions shown in Example 6-1, treated with the complex comprising the bioactive nucleic acid and the carrier peptide nucleic acid, and then cultured for 24, 48 and 72 hours. Next, 30 μL of RIPA buffer was added to each well to obtain a protein lysate. The protein lysate was quantified using the BCA assay kit (Thermo Fisher, USA), and 30 μg of the protein was separated by size through electrophoresis, transferred to a PVDF membrane, and then treated with TLR2 (SantaCruz Biotech., USA), MMP9 (SantaCruz Biotech., USA), p-NFkB (Cell Signaling Technology, USA), MyD88 (Cell Signaling Technology, USA) and TARC (Abcam, USA) as primary antibodies at a dilution of 1:1000, and then left to stand at 4° C. for one day. Next, the membrane was washed with 1×TBS-T, treated with Goat Anti-Rabbit and Goat Anti-mouse (SantaCruz Biotech., USA) as secondary antibodies at a dilution of 1:2000, and left to stand at room temperature for 2 hours. The membrane was treated with Supersignal™ West Femto Maximum Sensitivity Substrate (Thermo Fisher, USA), and the efficiency of inhibition of the target gene expression in the keratinocytes was analyzed using an Image 600 (Amersham, Germany) imager.

The nucleic acid complexes used in this Example are shown in Table 9 below.

TABLE 9

| Nucleic acid complexes for analysis of TLR2 expression in keratinocytes | |
|---|---|
| No. | Nucleic acid complex |
| 1 | SEQ ID NOs: 31 and 33 |
| 2 | SEQ ID NOs: 31 and 34 |
| 3 | SEQ ID NOs: 31 and 35 |
| 4 | SEQ ID NOs: 32 and 33 |
| 5 | SEQ ID NOs: 32 and 34 |
| 6 | SEQ ID NOs: 32 and 35 |

Figure 8B:
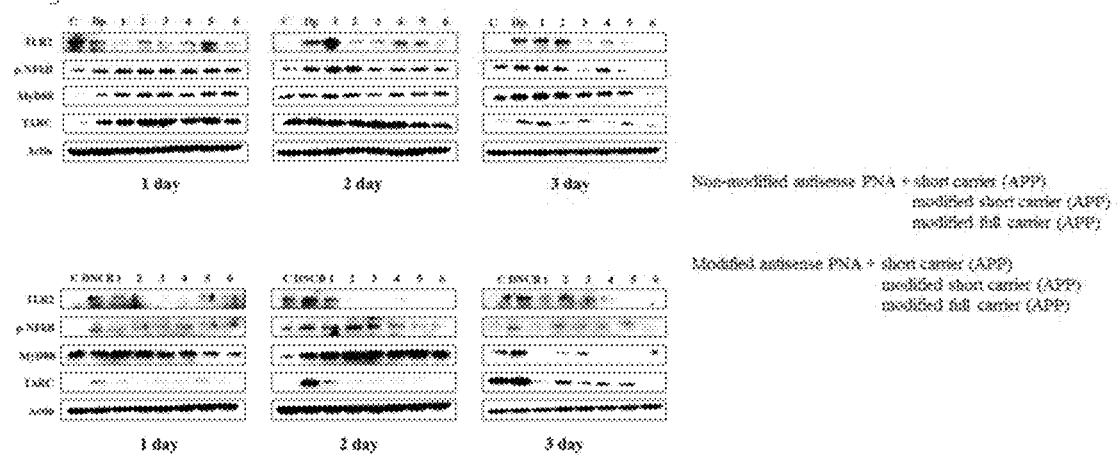

As a result, as shown in FIG. 8b, it was confirmed that expression of the target gene and downstream genes thereof was inhibited by the nucleic acid complex in a concentration-dependent manner with time.

Example 6-4: Analysis of Effect Against Atopic Dermatitis Phenotype in Atopic Dermatitis Animal Model Induced by House Dust Mite Extract and DNCB An animal model with atopic dermatitis induced by house dust mites was prepared by shaving the back of NC/Nga mice and applying 100 mg of AD cream (house dust mite extract cream, Biostir, Japan) twice a week for a total of 3 weeks. In addition, an animal model with atopic dermatitis induced by sick house syndrome was prepared by shaving the back of Balb/C mice and applying 50 μM DNCB twice a week for a total of 3 weeks. Each animal model was treated with a cream formulation of the nucleic complex a total of three times a week, and the phenotype in the atopic dermatitis animal model was analyzed in images, and the degree of hair growth on the back was measured by Image J.

The nucleic acid complexes used in this Example are shown in Table 10 below.

TABLE 10

| Nucleic acid complexes for analysis of atopic dermatitis phenotype | |
|---|---|
| Name | Nucleic acid complex |
| PNA 1 | SEQ ID NOs: 32 and 34 |
| PNA 2 | SEQ ID NOs: 32 and 35 |

Figure 8C:
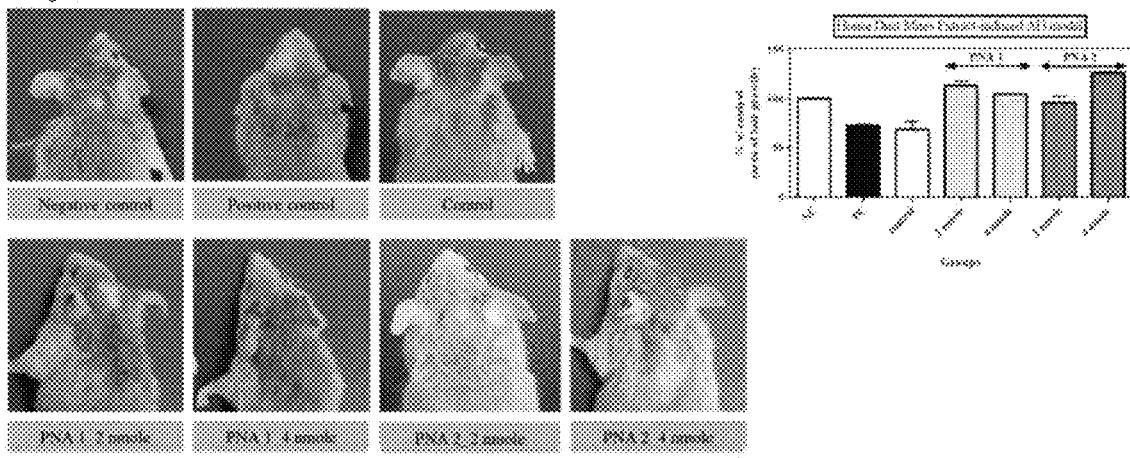
Figure 8D:
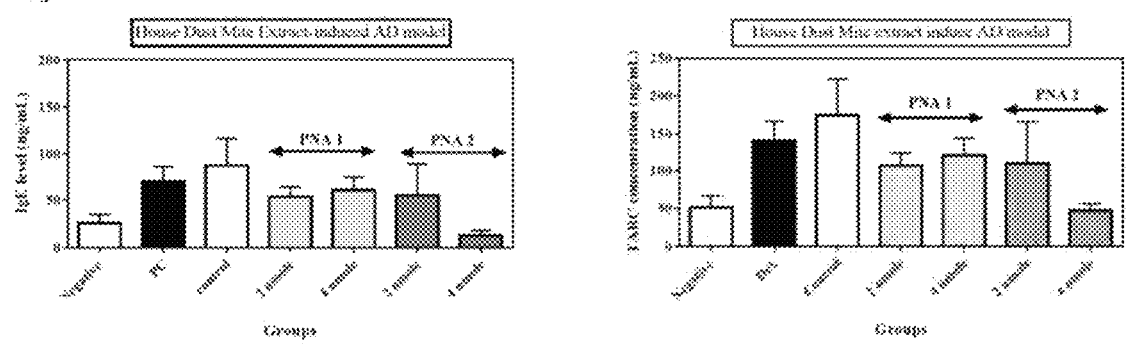
Figure 8E:
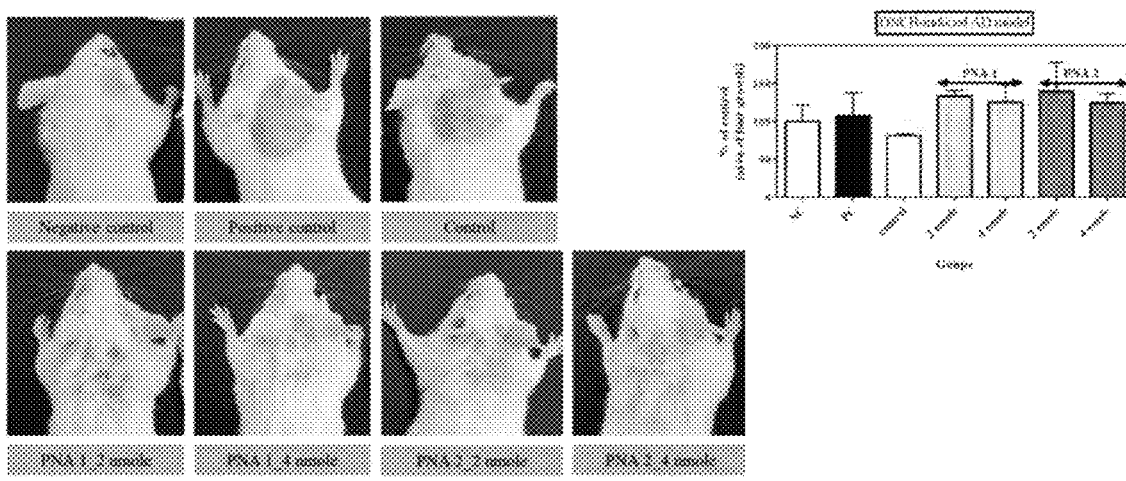

As shown in FIGS. 8c and 8e, it was confirmed that the atopic dermatitis phenotype decreased in the nucleic acid complex group.

Example 6-5: Analysis of Changes in IgE and TARC Concentrations in Serum

On the last day of the animal experiment performed under the conditions of Example 6-4, mouse blood is collected through the orbital vein, left to stand at room temperature for 2 hours or more, and centrifuged at 14,000 rpm for 15 min, and the serum was collected. The concentrations of IgE and TARC in the collected serum were measured using the experimental methods provided in an IgE ELISA kit (KOMABIOTECH Inc., Korea) and a TARC ELISA kit (R&D System, USA).

Figure 8F:
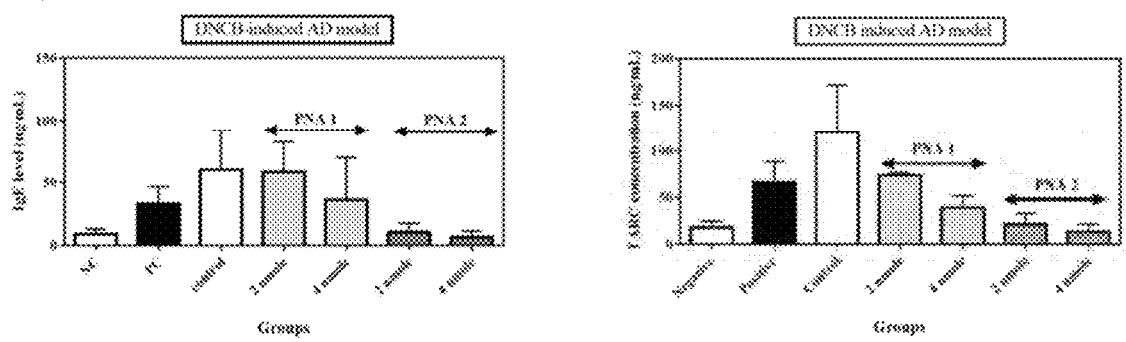

As a result, as shown in FIGS. 8d and 8f, it could be confirmed that the concentrations of IgE and TARC in the group treated with the nucleic acid complex decreased to levels similar to those in the negative control group, unlike those in the control group with induced atopic dermatitis.

Example 6-6: Analysis of Phenotype in Tissue of Atopic Dermatitis-Induced Animal Model by H&E Staining On the last day of the animal experiment performed under the conditions of Example 6-4, the mouse ear tissue was biopsied and fixed in 4% formalin solution for one day. The fixed tissue was embedded in paraffin, sectioned to 5 μm, and mounted on a glass slide. The mounted tissue was stained with Hematoxylin:Eoin staining solution for a predetermined time, washed with 1×PBS, and then analyzed with a microscope.

Figure 8G:
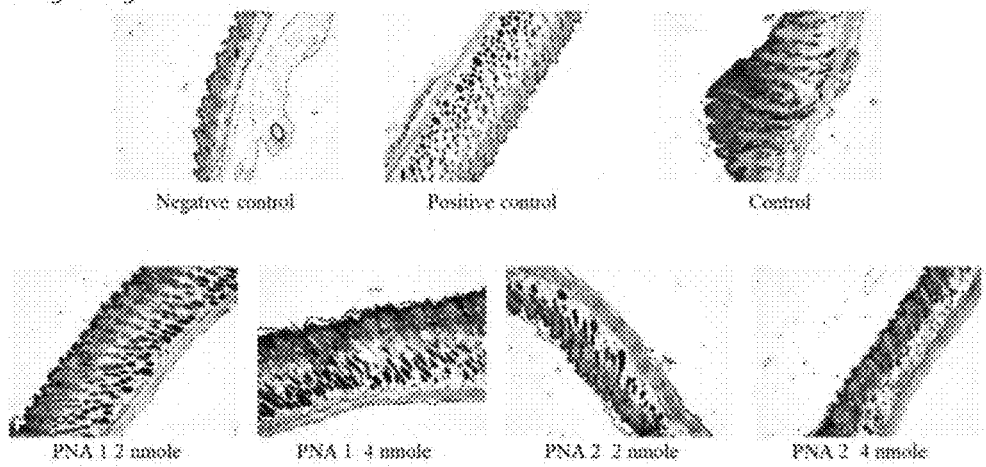
Figure 8H:
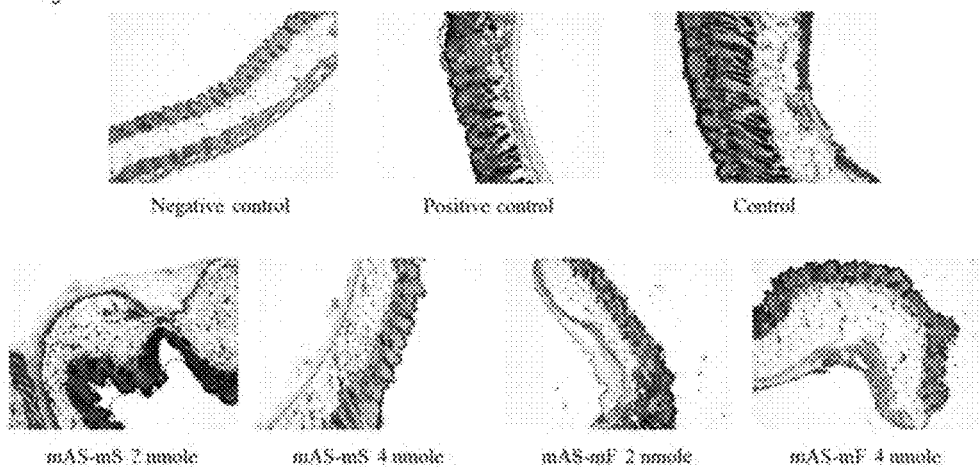

As a result, as shown in FIGS. 8g and 8h, abnormal growth of epidermis in the group treated with the nucleic acid complex decreased compared to that in the atopy-derived control group.

Example 6-7: Analysis of Inflammatory Marker in Tissue of Atopic Dermatitis-Induced Animal Model by Immunostaining On the last day of the experiment performed under the conditions of Example 6-4, the mouse back tissue was biopsied and fixed in 4% formalin solution for one day. The fixed tissue was embedded in paraffin, sectioned to 5 μm, and mounted on a glass slide. The mounted tissue was blocked in 0.5% BSA solution for 1 hour, treated with primary antibody solution against CD3 and CD11c, and incubated for one day. Next, the primary antibody solution was removed, and the remaining material was washed with 1×PBS, treated with secondary antibody solution, incubated at room temperature for 2 hours, and then analyzed by DAB staining.

Figure 8I:
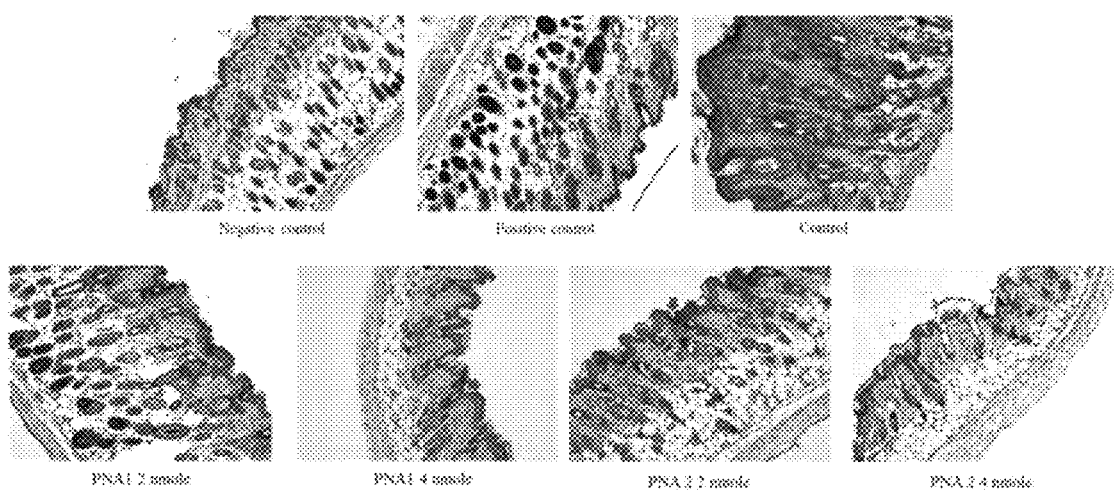
Figure 8J:
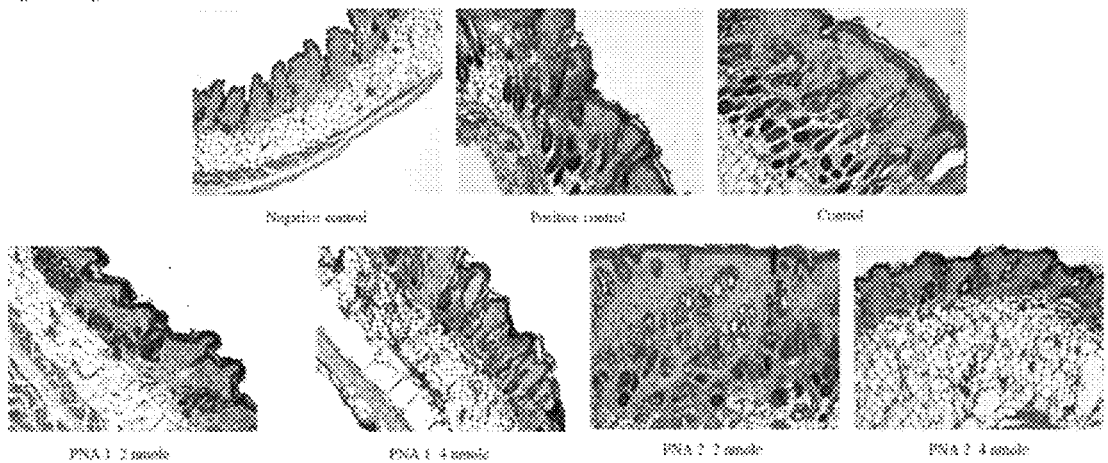

As a result, as shown in FIGS. 8i and 8j, it was confirmed that the inflammatory marker CD3 in the tissue decreased in the group treated with the nucleic acid complex compared to the atopic dermatitis-induced control group.

Examples 7: Analysis of Skin Regeneration Effect of Skin-Penetrating Carrier Containing Complex Having Structure of Structural Formula (1)

To analyze the skin regeneration effect of the nucleic acid complex, Smad3 was used as a target gene. Smad3 is a protein that is overexpressed in wounded skin, and is considered an important target in skin regeneration.

Example 7-1: Cell Culture

Human keratinocytes (HaCaT) obtained from the CLS (CLS Cell Lines Service, Germany) were cultured in DMEM culture medium (Dulbecco Modified Eagle Medium, Welgene, Korea) containing 10% (v/v) fetal bovine serum, 100 units/ml penicillin and 100 μg/ml streptomycin at 37° C. under 5% (v/v) $CO_2$. To analyze cell migration, the cells were treated with 5 ng/mL TGFβ-1 and cultured.

Example 7-2: Analysis of Effect of the Nucleic Acid Complex on Improvement in Cell Migration Ability by Wound-Healing Assay Human keratinocytes were seeded into a 12-well plate at a density $2\times10^4$ cells/well, treated with FBS-free medium, and cultured for 24 hours. The test was proceeded under the conditions described in Example 7-1, the culture cells were treated with the complex comprising the bioactive peptide nucleic acid and the carrier peptide nucleic acid, and treated with 5 ng/mL TGFβ-1, and cultured for 24 and 48 hours. Next, migration of the cells was analyzed with a microscope.

The nucleic acid complexes used in this Example are shown in Table 12 below.

TABLE 12

| Nucleic acid complexes for analysis of cell migration in keratinocytes | |
|---|---|
| Name | Nucleic acid complex |
| PNA 1 | SEQ ID NOs: 37 and 38 |
| PNA 2 | SEQ ID NOs: 37 and 39 |
| PNA 3 | SEQ ID NOs: 36 and 40 |

As a result, as shown in FIG. 9a, it was confirmed that cell migration in the nucleic acid complex-treated group was improved compared to that in the positive control group treated with TGFβ-1.

Example 7-3: Analysis of Gene Expression by Western Blot Assay

Human keratinocytes were seeded into a 6-well plate at a density of $1\times10^5$ cells/well, cultured for 24 hours. The test was proceeded under the conditions described in Example 7-1, treated with the complex comprising the bioactive nucleic acid and the carrier peptide nucleic acid, and then cultured for 24, 48 and 72 hours. Next, 30 μL of RIPA buffer was added to each well to obtain a protein lysate. The protein lysate was quantified using the BCA assay kit (Thermo Fisher, USA), and 30 μg of the protein was separated by size through electrophoresis, transferred to a PVDF membrane,

TABLE 11

Sequences of bioactive nucleic acids and carrier peptide nucleic acids for inhibiting Smad3 activity

| Component | SEQ ID NO | Nucleotide sequence | Monomer modification |
|---|---|---|---|
| Bioactive nucleic acid | SEQ ID NO: 36 | 5'-TG$^{(-)}$TCA$^{(+)}$AGCC$^{(-)}$ACT$^{(+)}$GC$^{(-)}$A-O-K-3 | -+-+- |
| | SEQ ID NO: 37 | 5'-GLFDIIKKIAESF-O-TG$^{(-)}$TCA$^{(+)}$AGCC$^{(-)}$ACT$^{(+)}$GC$^{(-)}$A-O-K-3 | -+-+- |
| Carrier peptide nucleic acid | SEQ ID NO: 38 | 5'-K-O-T$^{(+)}$GCA$^{(+)}$G-3' | ++ |
| | SEQ ID NO: 39 | 5'-K-O-T$^{(+)}$GCA$^{(+)}$G-O-Histidine(10)-3' | ++ |
| | SEQ ID NO: 40 | 5'-AC$^{(+)}$AGTTCGG(+)TGACG$^{(+)}$T-O-K | +++ |
| | SEQ ID NO: 41 | 5'-Histidine(10)-O-AC$^{(+)}$AGTTCGG$^{(+)}$TGACG$^{(+)}$T-O-K-3' | +++ | and then treated with p-smad3 (Cell Signaling Technology, USA) as primary antibody at a dilution of 1:1000, and then left to stand at 4° C. for one day. Next, the membrane was washed with 1×TBS-T, treated with Goat Anti-Rabbit (SantaCruz Biotech., USA) as secondary antibody at a dilution of 1:2000, and left to stand at room temperature for 2 hours. The membrane was treated with Supersignal™ West Femto Maximum Sensitivity Substrate (Thermo Fisher, USA), and the efficiency inhibition of the target gene expression in the keratinocytes was analyzed using an Image 600 (Amersham, Germany) imager.

The nucleic acid complexes used in this Example are shown in Table 13 below.

TABLE 13

Nucleic acid complexes for analysis of expression of smad3 protein and downstream genes in keratinocytes

| No. | Nucleic acid complex |
|---|---|
| 1 | SEQ ID NOs: 37 and 38 |
| 2 | SEQ ID NOs: 37 and 38 |
| 3 | SEQ ID NOs: 37 and 39 |
| 4 | SEQ ID NOs: 37 and 40 |
| 5 | SEQ ID NOs: 37 and 41 |
| 6 | SEQ ID NOs: 36 and 38 |
| 7 | SEQ ID NOs: 36 and 38 |
| 8 | SEQ ID NOs: 36 and 39 |
| 9 | SEQ ID NOs: 36 and 40 |
| 10 | SEQ ID NOs: 36 and 41 |

As a result, as shown in FIG. 9b, expression of the target gene and downstream genes thereof was inhibited by the nucleic acid complex in a concentration-dependent manner with time.

Example 8: Analysis of Keloid Treatment Effect of Skin-Penetrating Carrier Containing Complex Having Structure of Structural Formula (1)

To analyze the keloid treatment effect of the novel nucleic acid complex, TIEG1 was used as a target gene. TIEG1 is a protein that is overexpressed in the skin tissue of keloid patients, and is considered an important target in the treatment of keloids.

Example 8-1: Cell Culture

Keloid fibroblasts (KEL FIB) obtained from ATCC (American Type Culture Collection, USA) were cultured in DMEM culture medium (Dulbecco Modified Eagle Medium, Welgene, Korea) containing 10% (v/v) fetal bovine serum, 100 units/ml penicillin and 100 μg/ml streptomycin at 37° C. under 5% (v/v) $CO_2$.

Example 8-2: Analysis of Cell Viability in Keloid Fibroblasts by MTT Assay

Under the conditions described in Example 8-1, Keloid keratinocytes were seeded into a 96-well plate at a density of $6\times10^3$ cells/well, cultured for 24 hours, and then treated with the complexes produced to have the structure shown in Table 14, each comprising the bioactive nucleic acid and the carrier peptide nucleic acid. Next, each well was treated with 20 μL of MTT (3-(4,5-dimethylthiazol-2-yl)-2,5-diphenyltetrazolium bromide) solution prepared at a concentration of 5 mg/mL in 1×PBS. Next, each well was incubated for 4 hours, and then optical density (OD) was measured by a spectrophotometer and analyzed.

The nucleic acid complexes used in this Example are shown in Table 15 below.

TABLE 15

Nucleic acid complexes for analysis of cell viability in keloid fibroblasts

| No. | Nucleic acid complex |
|---|---|
| 1 | SEQ ID NOs: 42 and 44 |
| 2 | SEQ ID NOs: 42 and 45 |
| 3 | SEQ ID NOs: 42 and 46 |
| 4 | SEQ ID NOs: 42 and 47 |
| 5 | SEQ ID NOs: 43 and 44 |
| 6 | SEQ ID NOs: 43 and 45 |
| 7 | SEQ ID NOs: 43 and 46 |
| 8 | SEQ ID NOs: 43 and 47 |

As a result, as shown in FIG. 10a, it was confirmed that the cell viability in the keloid cells was decreased by the nucleic acid complex in a concentration-dependent manner.

Example 8-3: Analysis of Gene Expression by Western Blot Assay

Keloid keratinocytes were seeded into a 6-well plate at a density of $1\times10^5$ cells/well, cultured for 24 hours, the test was proceeded under the conditions described in Example 8-1, treated with the complex comprising the bioactive nucleic acid and the carrier peptide nucleic acid, and then cultured for 24, 48 and 72 hours. Next, 30 μL of RIPA buffer was added to each well to obtain a protein lysate. The protein lysate was quantified using the BCA assay kit (Thermo

TABLE 14

Sequences of Bioactive nucleic acid and carrier peptide nucleic acid for TIEG1 inhibition

| Component | SEQ ID NO | Nucleotide sequence | Monomer modification |
|---|---|---|---|
| Bioactive nucleic acid | SEQ ID NO: 42 | 5'-GC$^{(-)}$TTC$^{(+)}$TAC$^{(-)}$AG$^{(+)}$CTT$^{(-)}$CA-O-K-3' | -+-+- |
| | SEQ ID NO: 43 | GLFDIIKKIAESF-O-GC$^{(-)}$TTC$^{(+)}$TAC$^{(-)}$AG$^{(+)}$CTT$^{(-)}$CA-O-K | -+-+- |
| Carrier peptide nucleic acid | SEQ ID NO: 44 | 5'-K-O-TG$^{(+)}$AAGCTG$^{(+)}$TAGAA$^{(+)}$GC-3' | +++ |
| | SEQ ID NO: 45 | 5'-K-O-TG$^{(+)}$AAGCTG$^{(+)}$TAGAA$^{(+)}$GC-O-Histidine(10)-3' | +++ |
| | SEQ ID NO: 46 | 5'-CG$^{(+)}$AAGATG$^{(+)}$TCGAA$^{(+)}$GT-O-K-3' | +++ |
| | SEQ ID NO: 47 | 5'-Histidine(10)-O-CG$^{(+)}$AAGATG$^{(+)}$TCGAA$^{(+)}$GT-O-K-3' | +++ |

Fisher, USA), and 30 µg of the protein was separated by size through electrophoresis, transferred to a PVDF membrane, and then treated with TIEG1 (SantaCruz Biotech., USA), p-smad2 (SantaCruz Biotech., USA), smad7 (Cell Signaling Technology, USA) as primary antibodies at a dilution of 1:1000, and then left to stand at 4° C. for one day. Next, the membrane was washed with 1×TBS-T, treated with Goat Anti-Rabbit and Goat Anti-mouse (SantaCruz Biotech., USA) as secondary antibodies at a dilution of 1:2000, and left to stand at room temperature for 2 hours. The membrane was treated with Supersignal™ West Femto Maximum Sensitivity Substrate (Thermo Fisher, USA), and the efficiency of inhibition of the target gene expression in the keloid keratinocytes was analyzed using an Image 600 (Amersham, Germany) imager.

For the nucleic acid complexes shown in Table 14 above, the expression patterns of the TIEG1 gene and downstream genes thereof were analyzed. As a result, as shown in FIG. 10b, it was confirmed that expression of the target gene and downstream genes thereof was inhibited by the nucleic acid complex in a concentration-dependent manner with time.

INDUSTRIAL APPLICABILITY

According to the present invention, the skin-penetrating carrier containing the nucleic acid complex having the structure of Structural Formula (1) has both a skin penetration function of effectively delivering a large-molecular-weight drug and in vivo effectiveness.

In particular, the carrier according to the present invention enables bioactive nucleic acids or various compounds to pass through the stratum corneum, epidermis and/or dermis of the skin, thus, the carrier enables external treatment with a therapeutic drug for application to the skin surface and enables a desired drug to be delivered to an in vivo circulation system including blood.

Although the present invention has been described in detail with reference to specific features, it will be apparent to those skilled in the art that this description is only of a preferred embodiment thereof, and does not limit the scope of the present invention. Thus, the substantial scope of the present invention will be defined by the appended claims and equivalents thereto.

Sequence List Free Text

Electron file is attached.

The invention claimed is:

1. A skin-penetrating carrier containing a nucleic acid complex having a structure of the following Structural Formula (1):

[A≡C.sup.(+)] Structural Formula (1) wherein, A represents a bioactive nucleic acid having either a sequence capable of binding to a target gene or a target gene sequence; C represents a carrier peptide nucleic acid capable of binding to the bioactive nucleic acid; '≡' represents complementary binding between the bioactive nucleic acid and the carrier peptide nucleic acid; the bioactive nucleic acid represented by A is PNA (Peptide Nucleic Acid), and is generally negatively charged or neutral; C.sup.(+) indicates that the carrier peptide nucleic acid is generally positively charged; and the carrier peptide nucleic acid comprises one or more peptide nucleic acid monomers modified such that the carrier peptide nucleic acid is generally positively charged.

2. The skin-penetrating carrier of claim 1, wherein the nucleic acid complex has skin retention ability.

3. The skin-penetrating carrier of claim 1, wherein the nucleic acid complex further comprises a material for facilitating endosomal escape of the bioactive nucleic acid and the carrier peptide nucleic acid, and has a structure of the following Structural Formula (2):

[mA=mC.sup.(+)] Structural Formula (2) wherein, ‘m’ represents a material for facilitating endosomal escape of the bioactive nucleic acid and the carrier peptide nucleic acid.

4. The skin-penetrating carrier of claim 3, wherein the material for facilitating endosomal escape is bound to the 5'-end and/or 3'-end of each of the bioactive nucleic acid and the carrier peptide nucleic acid.

5. The skin-penetrating carrier of claim 3, wherein the material for facilitating endosomal escape is any one or more selected from the group consisting of peptides, lipid nanoparticles, polyplex nanoparticles, polymer nanospheres, inorganic nanoparticles, cationic lipid-based nanoparticles, cationic polymers, and pH-sensitive polymers.

6. The skin-penetrating carrier of claim 5, wherein the peptides are selected from the group consisting of GIGAVLKVLTTGLPALISWIKRKRQQ (SEQ ID NO: 48), GLFDIIKKIAESF (SEQ ID NO: 49), and histidine (10), the lipid nanoparticles are selected from the group consisting of lipids, phospholipids, cetyl palmitate, poloxamer 18, polyoxyethylenesorbitan trioleate, tristearin glyceride, and polyoxyethylenesorbitan monooleate, the polyplex nanoparticles are poly(amidoamine) or polyethylenimine (PEI), the polymer nanospheres are selected from the group consisting of polycaprolactone, poly(lactide-co-glycolide), polylactide, polyglycolide, poly(d,l-lactide), chitosan, and PLGA-polyethylene glycol, the inorganic nanoparticles are selected from the group consisting of $Fe_2O_3$ $Fe_3O_4$, $WO_3$, and $WO_{2.9}$, the cationic lipid-based nanoparticles are selected from the group consisting of 1-(aminoethyl)iminobis[N-(oleicylcysteinyl-1-amino-ethyl)propionamide], an N-alkylated derivative of PTA, and 3,5-didodecyloxybenzamidine, the cationic polymers are selected from the group consisting of vinylpyrrolidone/N,N-dimethylaminoethyl methacrylate acid copolymer diethyl sulphate, polyisobutylene, and poly(N-vinylcarbazole), and the pH-sensitive polymers are selected from the group consisting of polyacids, poly(acrylic acid), poly (methacrylic acid), and hydrolyzed polyacrylamide.

7. The skin-penetrating carrier of claim 1, wherein the nucleic acid complex further comprises any one or more selected from the group consisting of therapeutic proteins, therapeutic compounds, therapeutic compositions, cancer chemotherapeutic agents, toxins, cytotoxic substances, anti-inflammatory agents, arthritis treatment agents, growth factors, cytokines, chemokines, compounds for regulating one or more signaling pathways, antibodies, nucleic acids, nucleic acid analogs, cells, viruses, phages, virus particles, phage particles, virus capsids, phage capsids, virus-like particles, liposomes, micelles, beads, nanoparticles, microparticles, chemotherapeutic agents, contrast agents, imaging agents, labels, labeling agents, or combinations thereof.

8. The skin-penetrating carrier of claim 1, wherein the carrier peptide nucleic acid is composed of a nucleotide sequence which is partially or completely complementary to the bioactive nucleic acid.

9. The skin-penetrating carrier of claim 1, which is generally positively charged.

10. The skin-penetrating carrier of claim 1, wherein the carrier peptide nucleic acid comprises one or more gamma- or alpha-backbone-modified peptide nucleic acid monomers so as to be generally positively charged.

11. The skin-penetrating carrier of claim 10, wherein the gamma- or alpha-backbone-modified peptide nucleic acid monomers comprise a larger number of monomers having a positively charged amino acid than monomers having a negatively charged amino acid such that the carrier peptide nucleic acid is generally positively charged.

12. The skin-penetrating carrier of claim 10, wherein at least one substance selected from the group consisting of a hydrophobic moiety, a hydrophilic moiety, a target antigen-specific antibody, an aptamer, a quencher, a fluorescent marker and a luminescent marker is bound to the bioactive nucleic acid and/or the carrier peptide nucleic acid.

13. The skin-penetrating carrier of claim 1, wherein the binding between the bioactive nucleic acid and the carrier peptide nucleic acid is parallel binding or antiparallel binding according to 5'-directionality and 3'-directionality of each of the nucleic acids.

14. The skin-penetrating carrier of claim 1, wherein the binding affinity between the bioactive nucleic acid and the carrier peptide nucleic acid is lower than the binding affinity between the bioactive nucleic acid and a gene targeted by the bioactive nucleic acid.

15. The skin-penetrating carrier of claim 14, wherein the bioactive nucleic acid and the carrier peptide nucleic acid are bound to each other by parallel binding or partial specific binding so that the binding affinity between the bioactive nucleic acid and the carrier peptide nucleic acid is lower than the binding affinity between the bioactive nucleic acid and a gene targeted by the bioactive nucleic acid.

16. A composition for diagnosing diseases comprising the skin-penetrating carrier according to claim 1.

17. A composition for treating diseases comprising the skin-penetrating carrier according to claim 1.

18. The composition of claim 17, wherein the disease is skin disease.

19. The composition of claim 18, wherein a target gene, to which the bioactive nucleic acid contained in the skin-penetrating carrier binds, is any one or more selected from the group consisting of IFI16, TGFβR2, ERBB3, TLR2, smad3 and TIEG1, and the disease is skin disease.

20. The composition of claim 18, wherein the skin disease is any one selected from the group consisting of psoriasis, skin cancer, atopic dermatitis, skin damage, pigmentation, and keloid disease.

21. A formulation comprising the composition according to claim 17.

22. The formulation of claim 21, wherein the formulation is selected from the group consisting of an aqueous solution, a gel, an ointment, a cream, a lotion, a paste, a liniment, and a patch.

* * * * *

```
                         SEQUENCE LISTING

<160> NUMBER OF SEQ ID NOS: 49

<210> SEQ ID NO 1
<211> LENGTH: 15
<212> TYPE: DNA
<213> ORGANISM: Artificial Sequence
<220> FEATURE:
<223> OTHER INFORMATION: PNA

<400> SEQUENCE: 1
attcacatca gccac                                                        15

<210> SEQ ID NO 2
<211> LENGTH: 15
<212> TYPE: DNA
<213> ORGANISM: Artificial Sequence
<220> FEATURE:
<223> OTHER INFORMATION: PNA

<400> SEQUENCE: 2
attcacatca gccac                                                        15

<210> SEQ ID NO 3
<211> LENGTH: 15
<212> TYPE: DNA
<213> ORGANISM: Artificial Sequence
<220> FEATURE:
<223> OTHER INFORMATION: PNA

<400> SEQUENCE: 3
attcacatca gccac                                                        15

<210> SEQ ID NO 4
<211> LENGTH: 15
<212> TYPE: DNA
<213> ORGANISM: Artificial Sequence
<220> FEATURE:
<223> OTHER INFORMATION: PNA

<400> SEQUENCE: 4
attcacatca gccac                                                        15
```

-continued

```
<210> SEQ ID NO 5
<211> LENGTH: 15
<212> TYPE: DNA
<213> ORGANISM: Artificial Sequence
<220> FEATURE:
<223> OTHER INFORMATION: PNA

<400> SEQUENCE: 5
attcacatca gccac                                                    15

<210> SEQ ID NO 6
<211> LENGTH: 15
<212> TYPE: DNA
<213> ORGANISM: Artificial Sequence
<220> FEATURE:
<223> OTHER INFORMATION: PNA

<400> SEQUENCE: 6
attcacatca gccac                                                    15

<210> SEQ ID NO 7
<211> LENGTH: 15
<212> TYPE: DNA
<213> ORGANISM: Artificial Sequence
<220> FEATURE:
<223> OTHER INFORMATION: PNA

<400> SEQUENCE: 7
attcacatca gccac                                                    15

<210> SEQ ID NO 8
<211> LENGTH: 15
<212> TYPE: DNA
<213> ORGANISM: Artificial Sequence
<220> FEATURE:
<223> OTHER INFORMATION: PNA

<400> SEQUENCE: 8
attcacatca gccac                                                    15

<210> SEQ ID NO 9
<211> LENGTH: 15
<212> TYPE: DNA
<213> ORGANISM: Artificial Sequence
<220> FEATURE:
<223> OTHER INFORMATION: PNA

<400> SEQUENCE: 9
attcacatca gccac                                                    15

<210> SEQ ID NO 10
<211> LENGTH: 15
<212> TYPE: DNA
<213> ORGANISM: Artificial Sequence
<220> FEATURE:
<223> OTHER INFORMATION: PNA

<400> SEQUENCE: 10
gtggctgatg tgaat                                                    15

<210> SEQ ID NO 11
<211> LENGTH: 15
<212> TYPE: DNA
<213> ORGANISM: Artificial Sequence
<220> FEATURE:
<223> OTHER INFORMATION: PNA
```

-continued

```
<400> SEQUENCE: 11
taagtgtagt cggtg                                                    15

<210> SEQ ID NO 12
<211> LENGTH: 15
<212> TYPE: DNA
<213> ORGANISM: Artificial Sequence
<220> FEATURE:
<223> OTHER INFORMATION: PNA

<400> SEQUENCE: 12
taagtgtagt cggtg                                                    15

<210> SEQ ID NO 13
<211> LENGTH: 15
<212> TYPE: DNA
<213> ORGANISM: Artificial Sequence
<220> FEATURE:
<223> OTHER INFORMATION: PNA

<400> SEQUENCE: 13
taagtgtagt cggtg                                                    15

<210> SEQ ID NO 14
<211> LENGTH: 15
<212> TYPE: DNA
<213> ORGANISM: Artificial Sequence
<220> FEATURE:
<223> OTHER INFORMATION: PNA

<400> SEQUENCE: 14
taagtgtagt cggtg                                                    15

<210> SEQ ID NO 15
<211> LENGTH: 15
<212> TYPE: DNA
<213> ORGANISM: Artificial Sequence
<220> FEATURE:
<223> OTHER INFORMATION: PNA

<400> SEQUENCE: 15
taagtgtagt cggtg                                                    15

<210> SEQ ID NO 16
<211> LENGTH: 15
<212> TYPE: DNA
<213> ORGANISM: Artificial Sequence
<220> FEATURE:
<223> OTHER INFORMATION: PNA

<400> SEQUENCE: 16
taagtgtagt cggtg                                                    15

<210> SEQ ID NO 17
<211> LENGTH: 5
<212> TYPE: DNA
<213> ORGANISM: Artificial Sequence
<220> FEATURE:
<223> OTHER INFORMATION: PNA

<400> SEQUENCE: 17 cggtg                                                                5

<210> SEQ ID NO 18
<211> LENGTH: 7
```

```
<212> TYPE: DNA
<213> ORGANISM: Artificial Sequence
<220> FEATURE:
<223> OTHER INFORMATION: PNA

<400> SEQUENCE: 18 gtcggtg                                                              7

<210> SEQ ID NO 19
<211> LENGTH: 9
<212> TYPE: DNA
<213> ORGANISM: Artificial Sequence
<220> FEATURE:
<223> OTHER INFORMATION: PNA

<400> SEQUENCE: 19 tagtcggtg                                                            9

<210> SEQ ID NO 20
<211> LENGTH: 11
<212> TYPE: DNA
<213> ORGANISM: Artificial Sequence
<220> FEATURE:
<223> OTHER INFORMATION: PNA

<400> SEQUENCE: 20
tgtagtcggt g                                                        11

<210> SEQ ID NO 21
<211> LENGTH: 13
<212> TYPE: DNA
<213> ORGANISM: Artificial Sequence
<220> FEATURE:
<223> OTHER INFORMATION: PNA

<400> SEQUENCE: 21
agtgtagtcg gtg                                                      13

<210> SEQ ID NO 22
<211> LENGTH: 15
<212> TYPE: DNA
<213> ORGANISM: Artificial Sequence
<220> FEATURE:
<223> OTHER INFORMATION: PNA

<400> SEQUENCE: 22
attcacatca gccac                                                    15

<210> SEQ ID NO 23
<211> LENGTH: 5
<212> TYPE: DNA
<213> ORGANISM: Artificial Sequence
<220> FEATURE:
<223> OTHER INFORMATION: PNA

<400> SEQUENCE: 23 cggtg                                                                5

<210> SEQ ID NO 24
<211> LENGTH: 5
<212> TYPE: DNA
<213> ORGANISM: Artificial Sequence
<220> FEATURE:
<223> OTHER INFORMATION: PNA

<400> SEQUENCE: 24
```

```
gtggc                                                           5

<210> SEQ ID NO 25
<211> LENGTH: 15
<212> TYPE: DNA
<213> ORGANISM: Artificial Sequence
<220> FEATURE:
<223> OTHER INFORMATION: PNA

<400> SEQUENCE: 25
ggtcatccac agaca                                               15

<210> SEQ ID NO 26
<211> LENGTH: 15
<212> TYPE: DNA
<213> ORGANISM: Artificial Sequence
<220> FEATURE:
<223> OTHER INFORMATION: PNA

<400> SEQUENCE: 26
gacaatgata gtatt                                               15

<210> SEQ ID NO 27
<211> LENGTH: 5
<212> TYPE: DNA
<213> ORGANISM: Artificial Sequence
<220> FEATURE:
<223> OTHER INFORMATION: PNA

<400> SEQUENCE: 27 aatac                                                           5

<210> SEQ ID NO 28
<211> LENGTH: 15
<212> TYPE: DNA
<213> ORGANISM: Artificial Sequence
<220> FEATURE:
<223> OTHER INFORMATION: PNA

<400> SEQUENCE: 28
tgtctgtgga tgacc                                               15

<210> SEQ ID NO 29
<211> LENGTH: 15
<212> TYPE: DNA
<213> ORGANISM: Artificial Sequence
<220> FEATURE:
<223> OTHER INFORMATION: PNA

<400> SEQUENCE: 29
ctgttactat cataa                                               15

<210> SEQ ID NO 30
<211> LENGTH: 15
<212> TYPE: DNA
<213> ORGANISM: Artificial Sequence
<220> FEATURE:
<223> OTHER INFORMATION: PNA

<400> SEQUENCE: 30
aatactatca ttgtc                                               15

<210> SEQ ID NO 31
<211> LENGTH: 17
<212> TYPE: DNA
<213> ORGANISM: Artificial Sequence
```

```
<220> FEATURE:
<223> OTHER INFORMATION: PNA

<400> SEQUENCE: 31
atgtaggtga tcctgtt                                                17

<210> SEQ ID NO 32
<211> LENGTH: 17
<212> TYPE: DNA
<213> ORGANISM: Artificial Sequence
<220> FEATURE:
<223> OTHER INFORMATION: PNA

<400> SEQUENCE: 32
atgtaggtga tcctgtt                                                17

<210> SEQ ID NO 33
<211> LENGTH: 5
<212> TYPE: DNA
<213> ORGANISM: Artificial Sequence
<220> FEATURE:
<223> OTHER INFORMATION: PNA

<400> SEQUENCE: 33 aacag                                                              5

<210> SEQ ID NO 34
<211> LENGTH: 5
<212> TYPE: DNA
<213> ORGANISM: Artificial Sequence
<220> FEATURE:
<223> OTHER INFORMATION: PNA

<400> SEQUENCE: 34 aacag                                                              5

<210> SEQ ID NO 35
<211> LENGTH: 17
<212> TYPE: DNA
<213> ORGANISM: Artificial Sequence
<220> FEATURE:
<223> OTHER INFORMATION: PNA

<400> SEQUENCE: 35
tacaggatca cctacat                                                17

<210> SEQ ID NO 36
<211> LENGTH: 15
<212> TYPE: DNA
<213> ORGANISM: Artificial Sequence
<220> FEATURE:
<223> OTHER INFORMATION: PNA

<400> SEQUENCE: 36
tgtcaagcca ctgca                                                  15

<210> SEQ ID NO 37
<211> LENGTH: 15
<212> TYPE: DNA
<213> ORGANISM: Artificial Sequence
<220> FEATURE:
<223> OTHER INFORMATION: PNA

<400> SEQUENCE: 37
tgtcaagcca ctgca                                                  15
```

```
<210> SEQ ID NO 38
<211> LENGTH: 5
<212> TYPE: DNA
<213> ORGANISM: Artificial Sequence
<220> FEATURE:
<223> OTHER INFORMATION: PNA

<400> SEQUENCE: 38 tgcag                                                                    5

<210> SEQ ID NO 39
<211> LENGTH: 5
<212> TYPE: DNA
<213> ORGANISM: Artificial Sequence
<220> FEATURE:
<223> OTHER INFORMATION: PNA

<400> SEQUENCE: 39 tgcag                                                                    5

<210> SEQ ID NO 40
<211> LENGTH: 15
<212> TYPE: DNA
<213> ORGANISM: Artificial Sequence
<220> FEATURE:
<223> OTHER INFORMATION: PNA

<400> SEQUENCE: 40
acagttcggt gacgt                                                        15

<210> SEQ ID NO 41
<211> LENGTH: 15
<212> TYPE: DNA
<213> ORGANISM: Artificial Sequence
<220> FEATURE:
<223> OTHER INFORMATION: PNA

<400> SEQUENCE: 41
acagttcggt gacgt                                                        15

<210> SEQ ID NO 42
<211> LENGTH: 15
<212> TYPE: DNA
<213> ORGANISM: Artificial Sequence
<220> FEATURE:
<223> OTHER INFORMATION: PNA

<400> SEQUENCE: 42
gcttctacag cttca                                                        15

<210> SEQ ID NO 43
<211> LENGTH: 15
<212> TYPE: DNA
<213> ORGANISM: Artificial Sequence
<220> FEATURE:
<223> OTHER INFORMATION: PNA

<400> SEQUENCE: 43
gcttctacag cttca                                                        15

<210> SEQ ID NO 44
<211> LENGTH: 15
<212> TYPE: DNA
<213> ORGANISM: Artificial Sequence
<220> FEATURE:
<223> OTHER INFORMATION: PNA
```

```
<400> SEQUENCE: 44
tgaagctgta gaagc                                                  15

<210> SEQ ID NO 45
<211> LENGTH: 15
<212> TYPE: DNA
<213> ORGANISM: Artificial Sequence
<220> FEATURE:
<223> OTHER INFORMATION: PNA

<400> SEQUENCE: 45
tgaagctgta gaagc                                                  15

<210> SEQ ID NO 46
<211> LENGTH: 15
<212> TYPE: DNA
<213> ORGANISM: Artificial Sequence
<220> FEATURE:
<223> OTHER INFORMATION: PNA

<400> SEQUENCE: 46
cgaagatgtc gaagt                                                  15

<210> SEQ ID NO 47
<211> LENGTH: 15
<212> TYPE: DNA
<213> ORGANISM: Artificial Sequence
<220> FEATURE:
<223> OTHER INFORMATION: PNA

<400> SEQUENCE: 47
cgaagatgtc gaagt                                                  15

<210> SEQ ID NO 48
<211> LENGTH: 26
<212> TYPE: PRT
<213> ORGANISM: Artificial Sequence
<220> FEATURE:
<223> OTHER INFORMATION: peptide

<400> SEQUENCE: 48

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 49
<211> LENGTH: 13
<212> TYPE: PRT
<213> ORGANISM: Artificial Sequence
<220> FEATURE:
<223> OTHER INFORMATION: peptide

<400> SEQUENCE: 49

Gly Leu Phe Asp Ile Ile Lys Lys Ile Ala Glu Ser Phe
1               5                   10
```